(12) United States Patent
Girard et al.

(10) Patent No.: US 9,777,025 B2
(45) Date of Patent: Oct. 3, 2017

(54) SI-CONTAINING FILM FORMING PRECURSORS AND METHODS OF USING THE SAME

(71) Applicant: L'Air Liquide, Société Anonyme pour l'Etude et l'Exploitation des Procédés Georges Claude, Paris (FR)

(72) Inventors: Jean-Marc Girard, Versailles (FR); Peng Zhang, Montvale, NJ (US); Antonio Sanchez, Jersey City, NJ (US); Manish Khandelwal, Somerset, NJ (US); Gennadiy Itov, Flemington, NJ (US); Reno Pesaresi, Easton, PA (US)

(73) Assignee: L'Air Liquide, Société pour l'Etude et l'Exploitation des Procédés Georges Claude, Paris (FR)

(*) Notice: Subject to any disclaimer, the term of this patent is extended or adjusted under 35 U.S.C. 154(b) by 228 days.

(21) Appl. No.: 14/738,039

(22) Filed: Jun. 12, 2015

(65) Prior Publication Data

US 2015/0376211 A1 Dec. 31, 2015

Related U.S. Application Data

(60) Provisional application No. 62/140,248, filed on Mar. 30, 2015.

(51) Int. Cl.
| | | |
|---|---|---|
| *C01B 21/087* | (2006.01) | |
| *C23C 16/30* | (2006.01) | |
| *C07F 7/02* | (2006.01) | |
| *C01B 21/088* | (2006.01) | |
| *C23C 16/34* | (2006.01) | |
| *C23C 16/40* | (2006.01) | |
| *C23C 16/455* | (2006.01) | |
| *C23C 16/515* | (2006.01) | |

(52) U.S. Cl.
CPC ............ *C07F 7/025* (2013.01); *C01B 21/087* (2013.01); *C01B 21/088* (2013.01); *C23C 16/308* (2013.01); *C23C 16/345* (2013.01); *C23C 16/402* (2013.01); *C23C 16/45553* (2013.01); *C23C 16/515* (2013.01)

(58) Field of Classification Search
USPC ....................................................... 556/410
See application file for complete search history.

(56) References Cited

U.S. PATENT DOCUMENTS

| | | |
|---|---|---|
| 2,907,785 A | 10/1959 | Parshall |
| 3,532,728 A | 10/1970 | Fink |
| 4,200,666 A | 4/1980 | Reinberg |
| 4,675,424 A | 6/1987 | King, III |
| 4,720,395 A | 1/1988 | Foster |
| 4,882,256 A | 11/1989 | Osawa et al. |
| 5,047,526 A | 9/1991 | Yamamoto |
| 5,304,622 A | 4/1994 | Ikai et al. |
| 5,332,853 A | 7/1994 | Morrison et al. |
| 5,340,507 A | 8/1994 | Morrison et al. |
| 5,413,813 A | 5/1995 | Cruse et al. |
| 5,618,579 A | 4/1997 | Boire et al. |
| 5,663,398 A | 9/1997 | Schwindeman et al. |
| 5,874,368 A | 2/1999 | Laxman et al. |
| 5,932,286 A | 8/1999 | Beinglass et al. |
| 5,968,611 A | 10/1999 | Kaloyeros et al. |
| 6,333,547 B1 | 12/2001 | Tanaka et al. |
| 6,365,231 B2 | 4/2002 | Sato et al. |
| 6,503,557 B1 | 1/2003 | Joret |
| 6,566,281 B1 | 5/2003 | Buchanan et al. |
| 6,630,413 B2 | 10/2003 | Todd |
| 6,645,884 B1 | 11/2003 | Yang et al. |
| 6,821,825 B2 | 11/2004 | Todd et al. |
| 6,936,548 B2 | 8/2005 | Dussarrat et al. |
| 7,122,222 B2 | 10/2006 | Xiao et al. |
| 7,192,626 B2 | 3/2007 | Dussarrat et al. |
| 7,259,250 B2 | 8/2007 | Stamler et al. |
| 7,510,984 B2 | 3/2009 | Saito et al. |
| 7,638,645 B2 | 12/2009 | Gordon et al. |
| 7,838,329 B2 | 11/2010 | Hunks et al. |
| 8,173,554 B2 | 5/2012 | Lee et al. |
| 8,236,381 B2 | 8/2012 | Okubo |
| 8,318,584 B2 | 11/2012 | Li et al. |
| 8,357,430 B2 | 1/2013 | Dussarrat et al. |
| 8,501,762 B2 | 8/2013 | Li et al. |
| 8,669,387 B2 * | 3/2014 | Miller ...................... B01J 4/002 556/400 |
| 8,846,538 B1 | 9/2014 | Chen et al. |

(Continued)

FOREIGN PATENT DOCUMENTS

| | | |
|---|---|---|
| DE | 1 158 972 | 12/1963 |
| EP | 0 525 881 | 2/1993 |
| EP | 1 441 042 | 7/2004 |
| EP | 2 000 561 | 12/2008 |
| GB | 1 006 803 | 10/1965 |
| JP | S61 234534 | 10/1986 |
| JP | H06 338497 | 12/1994 |
| JP | 2001 168092 | 6/2001 |
| JP | H13 358139 | 12/2001 |
| JP | 2002 009072 | 1/2002 |

(Continued)

OTHER PUBLICATIONS

"Reaction of Silylphosphine with Ammonia" authored by Norman et al. and published in Inorg. Chem. (1979) 18(6), 1594-1597.*

(Continued)

*Primary Examiner* — Marc Zimmer
(74) *Attorney, Agent, or Firm* — Patricia E. McQueeney

(57) ABSTRACT

Mono-substituted TSA precursor Si-containing film forming compositions are disclosed. The precursors have the formula: $(SiH_3)_2N—SiH_2—X$, wherein X is selected from a halogen atom; an isocyanato group; an amino group; an N-containing $C_4$-$C_{10}$ saturated or unsaturated heterocycle; or an alkoxy group. Methods for forming the Si-containing film using the disclosed mono-substituted TSA precursor are also disclosed.

27 Claims, 4 Drawing Sheets

(56) References Cited

U.S. PATENT DOCUMENTS

| | | |
|---|---|---|
| 2001/0024867 A1 | 9/2001 | Saida et al. |
| 2001/0048973 A1 | 12/2001 | Sato et al. |
| 2002/0016084 A1 | 2/2002 | Todd |
| 2003/0203653 A1 | 10/2003 | Buchanan et al. |
| 2004/0194706 A1 | 10/2004 | Wang et al. |
| 2005/0070717 A1 | 3/2005 | Wasserscheid et al. |
| 2005/0085098 A1 | 4/2005 | Timmermans et al. |
| 2005/0136693 A1 | 6/2005 | Hasebe et al. |
| 2005/0142716 A1 | 6/2005 | Nakajima et al. |
| 2005/0181633 A1 | 8/2005 | Hochberg et al. |
| 2005/0196977 A1 | 9/2005 | Saito et al. |
| 2006/0222583 A1 | 10/2006 | Hazeltine |
| 2006/0286817 A1 | 12/2006 | Kato et al. |
| 2007/0010072 A1 | 1/2007 | Bailey et al. |
| 2007/0078252 A1 | 4/2007 | Dioumaev |
| 2007/0123733 A1 | 5/2007 | Boerner et al. |
| 2008/0045723 A1 | 2/2008 | Cassol et al. |
| 2008/0241575 A1 | 10/2008 | Lavoie et al. |
| 2008/0268642 A1 | 10/2008 | Yanagita et al. |
| 2009/0075490 A1 | 3/2009 | Dussarrat |
| 2009/0137100 A1 | 5/2009 | Xiao et al. |
| 2009/0256127 A1 | 10/2009 | Feist et al. |
| 2009/0291872 A1 | 11/2009 | Bara et al. |
| 2009/0291874 A1 | 11/2009 | Bara et al. |
| 2009/0299084 A1 | 12/2009 | Okubo et al. |
| 2009/0321733 A1 | 12/2009 | Gatineau et al. |
| 2010/0104755 A1 | 4/2010 | Dussarrat et al. |
| 2010/0221428 A1 | 9/2010 | Dussarrat |
| 2011/0183502 A1 | 7/2011 | Dioumaev |
| 2012/0017934 A1 | 1/2012 | Kumon et al. |
| 2012/0058282 A1 | 3/2012 | Hong et al. |
| 2012/0213940 A1 | 8/2012 | Mallick |
| 2012/0220139 A1 | 8/2012 | Lee et al. |
| 2013/0089487 A1 | 4/2013 | Ritter, III |
| 2013/0143018 A1 | 6/2013 | Tan et al. |
| 2013/0189854 A1 | 7/2013 | Hausmann et al. |
| 2013/0224097 A1 | 8/2013 | Miller |
| 2013/0323435 A1 | 12/2013 | Xiao et al. |
| 2014/0051264 A1 | 2/2014 | Mallick et al. |
| 2014/0057458 A1 | 2/2014 | Park et al. |
| 2014/0158580 A1 | 6/2014 | Xiao et al. |
| 2014/0193983 A1 | 7/2014 | Lavoie |
| 2014/0363985 A1 | 12/2014 | Jang et al. |
| 2015/0246937 A1 | 9/2015 | Xiao et al. |
| 2016/0237099 A1* | 8/2016 | Sanchez ................ C07F 7/025 |

FOREIGN PATENT DOCUMENTS

| | | |
|---|---|---|
| JP | 2004 119629 | 4/2004 |
| JP | 2005 251877 | 9/2005 |
| JP | 2006 16641 | 1/2006 |
| KR | 10 2012 0024473 | 3/2012 |
| KR | 10 2012 0099270 | 9/2012 |
| KR | 10 2013 0135793 | 12/2013 |
| KR | 10 2014 0057908 | 5/2014 |
| WO | WO 03 045959 | 6/2003 |
| WO | WO 03 046253 | 6/2003 |
| WO | WO 2005 045899 | 5/2005 |
| WO | WO 2006 136584 | 12/2006 |
| WO | WO 2007 008705 | 1/2007 |
| WO | WO 2007 112779 | 10/2007 |
| WO | WO 2007 112780 | 10/2007 |
| WO | WO 2009 081383 | 7/2009 |
| WO | WO 2009 087609 | 7/2009 |
| WO | WO 2011 056519 | 5/2011 |
| WO | WO2013 058061 | 4/2013 |
| WO | WO 2014 196827 | 12/2014 |
| WO | WO 2015/047914 A1 * | 4/2015 |
| WO | WO 2015 190749 | 12/2015 |

OTHER PUBLICATIONS

Acres, G.J.K. et al., "The design and preparation of supported catalysts," Catalysis 4 (1981): 1-30.

Andreev, A.A. et al., "Direct electrophilic silylation of terminal alkynes," Organic Letters 2004, vol. 6, No. 3, pp. 421-424 and SI1-SI5.

Caliman, V., "The wide synthetic versatility of five membered rings containing phosphorus," Quimica Nova, 23(3) (2000), 346-356.

Copel, M. et al., "Nucleation of chemical vapor deposited silicon nitride on silicon dioxide," Aplied Physics Letters, vol. 74, No. 13, Mar. 29, 1999, 1830-1832.

DNF, "Semiconductor material," 2013. Retrieved from the Internet: http://www.dnfsolution.com/eng/sub02/sub01_13.html.

Felch, S.B. et al., "Plasma doping for the fabrication of ultra-shallow junctions," Surface and Coatings Technology 156 (2002) 229-236.

Fessenden, R. et al., "An extension of and the reversibility of the silylamine-amine exchange reaction," J. Org. Chem. 1961, 26 (11), 4638-4641.

Fluck, E. et al., "Coordination compounds with 3-, 4- and 6-membered heterocycles containing phosphorus," Pure & Appl. Chem., 1998, vol. 70, No. 4, 819-826.

Godleski, S.A., et al., "MNDO study of phosphine- and amine-substituted silicenium ions", Tetrahedron Letter (1982), 23(43) 4453-3356.

Grow, J.M. et al., "Growth kinetics and characterization of low pressure chemically vapor deposited $Si_3N_4$ films from $(C_4H_9)_2$ $SiH_2$ and $NH_3$," Material Letters, vol. 23, 1995, 187-193.

Gumpher, J. et al., "Characterization of low-temperature silicon nitride LPCVD from bis(tertiarybutylamino)silane and ammonia," J. Electrochem. Soc., 2004, vol. 151, No. 5, G353-G359.

Ishii, K. et al., "Growth of polycrystalline hexagonal-close-packed Co films on glass substrates from low kinetic energy vapor," Journal of Vacuum Science & Technology A 16 (1998), 759-762.

Laine, R.M., "Transition metal catalysed synthesis of oligo- and polysilazanes," Platinum Metals Rev., 1988, 32(2), 64-71.

Lee, J. et al., "A hydrogen gas sensor employing vertically aligned $TiO_2$ nanotube arrays," Sensors and Actuators B 160 (2011) 1494-1498.

Levy, R.A. et al., "Low pressure chemical vapor deposition of silicon nitride using the environmentally friendly tris(dimethylamino)silane precursor," M. Mater. Res., vol. 11, No. 6, Jun. 1996, 1483-1488.

Liptrot, D.J. et al., "Beyond dehydrocoupling: Group 2 mediated boron-nitrogen desilacoupling," Angew. Chem. Inist. Ed. 2015, 54, 15280-15283.

Liu, H.Q. et al., "Dehydrocoupling of ammonia and silanes catalyzed by dimethyltitanocene," Organometallics 1992, 11, 822-827.

Mitzel, N.W., "Simple silylhydrazines as models for Si—N β-donor interactions in SiNN units," Chem. Eur. J., 1998, 4, No. 4, 692-698.

Pereira, M.A. et al., "Silicon nitride deposited by ECR-CVD at room temperature for LOCOS isolation technology," Applied Surface Science 212-213 (2003), pp. 388-392.

Roering, A.J. et al., "Zirconium-catalyzed heterodehydrocoupling of primary phosphines with silanes and germanes," Inorganic Chemistry 2007, 46(17), 6855-6857 Abstract.

Scantlin, W.M., et al., "The borane-catalyzed condensation of trisilazane and N-methyldisilazane", Inorganic Chemistry (1972), 11(12), 3028-2084.

Scantlin, W.M., et al., "Pentaborane(9)-catalyzed condensation of silylamines", Journal of the Chemical Society D: Chemical Communications (1971), (20), 1246.

Schmidbauer, H. et al., "Difference in reactivity of 1,4-disilabutane and n-tetrasilane towards secondary amines," Z. Naturforsch. 45b, 1990, 1679-1863.

Schuh, H. et al., "Disilanyl-amines: Compounds comprising the structural unit Si—Si—N, as single-source precursors for plasma-enhanced chemical vapour deposition (PE-CVD) of silicon nitride," Z. Anorg. Allg. Chem. 619 (1993) 1347-1352.

Smirnova, T.P. et al., "SiCN alloys obtained by remote plasma chemical vapour deposition from novel precursors," Preparation and Characterization, Elsevier Sequoia, NL, vol. 429, No. 1-2, Apr. 1, 2003, 144-151.

(56) References Cited

OTHER PUBLICATIONS

Söldner, M. et al., "1,2-disilanediyl bis(triflate), F(3)CSO(3)—SiH(2)—O(3)SCF(3) as the key intermediate for a facile preparation of open-chain and cyclic 1,1- and 1,2-diaminodisilanes," Inorg. Chem. Apr. 23, 1997, 36(9), 1758-1763.
Sommer, L.H. et al, "Stereochemistry of asymmetric silicon. XVI. Transition metal catalyzed substitute reactions of optically active organosilicon hydrides," Journal of the American Chemical Society, 91:25, Dec. 3, 1969, 7061-7067.
Takaki, K. et al., "Dehydrogenative silylation of amines and hydrosilylation of imines catalyzed by ytterbium-imine complexes," J. Org. Chem. 1999, 64, 3891-3895.
Taniguchi, K., et al., "Heterogeneous-Gold-Catalyzed Acceptorless Cross-Dehydrogenative Coupling of Hydrosilanes and Isocyanic Acid Generated in situ from Urea", Angew. Chem. Int. Ed. 2013, 52, 1-5.
Toh, C.K. et al., "Ruthenium carbonyl-catalysed Si-heteroatom X coupling (X=S, O, N)," Journal of Organometallic Chemistry 717 (2012) 9-13.
Wells, R.I. et al., "Studies of silicon-nitrogen compounds. The base-catalyzed elimination of silane from trisilylamine," Journal of American Chemical Society 88:1, Jan. 5, 1966, 1-6.
Yota, J. et al., "A comparative study on inductively-coupled plasma high-density plasma, plasma-enhanced, and low pressure chemical vapor deposition silicon nitride films," J. Vac. Sci. Technol. A 18(2), Mar./Apr. 2000, pp. 372-376.
International Search Report and Written Opinion for corresponding PCT/US2016/025010, Jul. 15, 2016.
International Search Report and Written Opinion for corresponding PCT/US2016/037006, Sep. 12, 2016.
International Search Report and Written Opinion for corresponding PCT/US2016/037013, Sep. 12, 2016.
International Search Report for related PCT/EP2003/012395, Feb. 18, 2004.
International Search Report and Written Opinion for related PCT/IB2004/001346, Oct. 19, 2004.
International Search Report and Written Opinion for related PCT/EP2005/054064, Nov. 24, 2005.
International Search Report and Written Opinion for related PCT/US2014/056618, Dec. 12, 2014.
International Search Report and Written Opinion for related PCT/US2014/057377, Feb. 19, 2015.
Cradock, S. et al., "Reactions of tin(IV) chloride with silyl compounds. I. Reactions with inorganic silyl compounds," Journal of the Chemical Society Dalton Transcations, Jan. 1975, 1624-1628.

\* cited by examiner

SI-CONTAINING FILM FORMING PRECURSORS AND METHODS OF USING THE SAME

CROSS REFERENCE TO RELATED APPLICATIONS

The present application claims the benefit of U.S. Provisional Application Ser. No. 62/140,248 filed Mar. 30, 2015, herein incorporated by reference in its entirety for all purposes.

TECHNICAL FIELD

Disclosed are Si-containing film forming compositions comprising mono-substituted trisilylamine precursors, methods of synthesizing the same, and methods of using the same to deposit Si-containing films using vapor deposition processes for manufacturing semiconductors, photovoltaics, LCD-TFT, flat panel-type devices, refractory materials, or aeronautics.

BACKGROUND

A variety of silicon containing precursor have been used to deposit Si-containing thin films on various substrates by vapor deposition processes. The choice of the suitable silicon precursor and, when applicable, of the co-reactant are generally driven by the target film composition and properties, as well as by the constraints brought by the substrate on which the film is to be deposited. Some substrates may require low temperature deposition processes. For instance, deposition on plastic substrates or Si substrates coated with organic films may require deposition temperatures below 100° C. (i.e., 20° C.-100° C.), while maintaining a reasonable deposition rate to be of industrial interest. Such films may be used as spacer-defined lithography application in semiconductor fabrication, but also for sealing organic light-emitting diode (OLED) devices or creating moisture diffusion barriers on films. Similar constraints at different temperature ranges appear in the different steps of semiconductor manufacturing, such as, capping layers over metals, gate spacers, etc.

Trisilylamine (TSA) is a molecule with a high Si content and has the formula of $N(SiH_3)_3$. TSA may be used as a low temperature (T) silicon nitride precursor (see, e.g., U.S. Pat. No. 7,192,626), as well as a precursor for flowable CVD (see, e.g., U.S. Pat. No. 8,846,536, US 2014/0057458 or U.S. Pat. No. 8,318,584). However, while TSA appears as a versatile precursor (Carbon-free and low T capability) for a variety of thin film deposition processes, it's applicability to thermal ALD has been limited (see, e.g., U.S. Pat. No. 8,173,554, indicating that plasma activation is necessary to obtain a meaningful growth per cycle).

US201410363985 A1 discloses amino-silylamines used for forming a silicon-containing thin-film having a generic formula of $R^1R^2R^3Si—N(SiR^4R^5—NR^6R^7)_2$, wherein $R^1$ to $R^5$ are each independently hydrogen, halogen, (C1-C7)alkyl, (C2-C7)alkenyl, (C2-C7)alkynyl, (C3-C7)cycloalkyl or (C6-C12)aryl. US2014/0158580A describes an alkoxysilylamine having a TSA-like structure. U.S. Pat. No. 7,122,222 uses a Si—C bond free hydrazinosilane precursor $[R^1_2N—NH]_nSi(R^2)_{4-n}$ to deposit SiN, $SiO_2$ and SiON films. Silazane compounds $N—(SiR^1R^2R^3)_mR^4_{3-m}$ disclosed in WO2013/058061 are used as a coating gas. $(RR^1R^2M^a)_yA(R^3)_x$ disclosed in U.S. Pat. No. 5,332,853 is used as a catalytic compound to produce a functionalized alkylalkali metal compound. Similar patents include U.S. Pat. No. 5,663,398A, U.S. Pat. No. 5,332,853A, U.S. Pat. No. 5,340,507A, EP 525881 A1, etc.

As such, industries using vapor-based deposition processes such as CVD or ALD (in all possible meanings, such as LPCVD, SACVD, PECVD, PEALD, etc.) are still looking for precursors that are ideal for their applications, i.e. having the highest possible deposition rates within the constraints of their processes, substrates and film targets.

SUMMARY

Disclosed are Si-containing film forming compositions comprising a mono-substituted TSA precursor having the formula $(SiH_3)_2NSiH_2—X$, wherein X is a halogen atom selected from Cl, Br or I; an isocyanato group [—NCO]; an amino group [—$NR^1R^2$]; a N-containing $C_4$-$C_{10}$ saturated or unsaturated heterocycle; or an alkoxy group [—O—R]; $R^1$, $R^2$ and R is selected from H; a silyl group [—$SiR'_3$]; or a $C_1$-$C_6$ linear or branched, saturated or unsaturated hydrocarbyl group; with each R' being independently selected from H; a halogen atom selected from Cl, Br, or I; a $C_1$-$C_4$ saturated or unsaturated hydrocarbyl group; a $C_1$-$C_4$ saturated or unsaturated alkoxy group; or an amino group [—$NR^3R^4$] with each $R^3$ and $R^4$ being independently selected from H and a $C_1$-$C_6$ linear or branched, saturated or unsaturated hydrocarbyl group, provided that if $R^1$=H, then $R^2 \neq$H, Me or Et. The disclosed Si-containing film forming compositions may include one or more of the following aspects:

- the mono-substituted TSA precursor wherein X is a halogen atom;
- the mono-substituted TSA precursor being $(SiH_3)_2N—SiH_2—Cl$;
- the mono-substituted TSA precursor being $(SiH_3)_2N—SiH_2—Br$;
- the mono-substituted TSA precursor being $(SiH_3)_2N—SiH_2—I$;
- the mono-substituted TSA precursor wherein X is a isocyanate —NCO (i.e., being $(SiH_3)_2N—SiH_2—NCO$);
- the mono-substituted TSA precursor wherein X is an amino group [—$NR^1R^2$];
- the mono-substituted TSA precursor being $(SiH_3)_2N—SiH_2—NiPr_2$;
- the mono-substituted TSA precursor being $(SiH_3)_2N—SiH_2—NHiPr$;
- the mono-substituted TSA precursor being $(SiH_3)_2N—SiH_2—NHtBu$;
- the mono-substituted TSA precursor not being $(SiH_3)_2—N—SiH_2—N(SiH_3)(SiH_2(NHEt))$ (i.e., when $X=NR^1R^2$ and $R^1$ is $SiH_3$ and $R^2$ is NHEt);
- the mono-substituted TSA precursor being $(SiH_3)_2N—SiH_2NEt_2$;
- the mono-substituted TSA precursor being $(SiH_3)_2N—SiH_2NEtMe$;
- the mono-substituted TSA precursor being $(SiH_3)_2N—SiH_2NMe_2$;
- the mono-substituted TSA precursor being $(SiH_3)_2N—SiH_2NMeiPr$;
- the mono-substituted TSA precursor being $(SiH_3)_2N—SiH_2NEtiPr$;
- the mono-substituted TSA precursor wherein X is $N(SiR_3)_2$, wherein each R is independently selected from a halogen, H, or a $C_1$-$C_4$ alkyl group;
- the mono-substituted TSA precursor being $(SiH_3)_2N—SiH_2—N(SiCl_3)_2$;

the mono-substituted TSA precursor being (SiH$_3$)$_2$N—SiH$_2$—N(SiBr$_3$)$_2$;
the mono-substituted TSA precursor being (SiH$_3$)$_2$N—SiH$_2$—N(SiI$_3$)$_2$;
the mono-substituted TSA precursor being (SiH$_3$)$_2$N—SiH$_2$—N(SiH$_3$)$_2$;
the mono-substituted TSA precursor being (SiH$_3$)$_2$—N—SiH$_2$—N(SiH$_3$)(SiH$_2$Cl);
the mono-substituted TSA precursor being (SiH$_3$)$_2$—N—SiH$_2$—N(SiH$_3$)(SiH$_2$(NEt$_2$);
the mono-substituted TSA precursor being (SiH$_3$)$_2$—N—SiH$_2$—N(SiH$_3$)(SiH$_2$(NiPr$_2$);
the mono-substituted TSA precursor being (SiH$_3$)$_2$—N—SiH$_2$—N(SiH$_3$)(SiH$_2$(NHtBu);
the mono-substituted TSA precursor being (SiH$_3$)$_2$—N—SiH$_2$—N(SiH$_3$)(SiH$_2$OEt);
the mono-substituted TSA precursor being (SiH$_3$)$_2$—N—SiH$_2$—N(SiH$_3$)(SiH$_2$OiPr);
the mono-substituted TSA precursor being (SiH$_3$)$_2$N—SiH$_2$—N(SiMe$_3$)$_2$;
the mono-substituted TSA precursor being (SiH$_3$)$_2$N—SiH$_2$—NH(SiMe$_3$);
the mono-substituted TSA precursor being (SiH$_3$)$_2$N—SiH$_2$—N(SiEt$_3$)$_2$;
the mono-substituted TSA precursor being (SiH$_3$)$_2$—N—SiH$_2$—N(SiMe$_2$Et)$_2$;
the mono-substituted TSA precursor being (SiH$_3$)$_2$—N—SiH$_2$—N(SiMe$_2$iPr)$_2$;
the mono-substituted TSA precursor being (SiH$_3$)$_2$—N—SiH$_2$—N(SiMe$_2$nPr)$_2$;
the mono-substituted TSA precursor wherein X is a N-containing C$_4$-C$_{10}$ heterocycle;
the mono-substituted TSA precursor wherein the N-containing C$_4$-C$_{10}$ heterocycle is selected from pyrrolidine, pyrrole, and piperidine;
the mono-substituted TSA precursor being (SiH$_3$)$_2$N—SiH$_2$-(pyrrolidine);
the mono-substituted TSA precursor being (SiH$_3$)$_2$N—SiH$_2$-(pyrrole);
the mono-substituted TSA precursor being (SiH$_3$)$_2$N—SiH$_2$-(piperidine);
the mono-substituted TSA precursor wherein X is an alkoxy group [—O—R];
the mono-substituted TSA precursor being (SiH$_3$)$_2$N—SiH$_2$—(OH);
the mono-substituted TSA precursor being (SiH$_3$)$_2$N—SiH$_2$—(OMe);
the mono-substituted TSA precursor being (SiH$_3$)$_2$N—SiH$_2$—(OEt);
the mono-substituted TSA precursor being (SiH$_3$)$_2$N—SiH$_2$—(OiPr);
the mono-substituted TSA precursor being (SiH$_3$)$_2$N—SiH$_2$—(OnPr);
the mono-substituted TSA precursor being (SiH$_3$)$_2$N—SiH$_2$—(OtBu);
the mono-substituted TSA precursor wherein X is —O—SiR$_3$ and each R is independently selected from H, a halogen, or a C$_1$-C$_4$ hydrocarbyl group;
the mono-substituted TSA precursor being (SiH$_3$)$_2$N—SiH$_2$—(OSiH$_3$);
the mono-substituted TSA precursor being (SiH$_3$)$_2$N—SiH$_2$—(OSiCl$_3$);
the mono-substituted TSA precursor being (SiH$_3$)$_2$N—SiH$_2$—(OSiBr$_3$);
the mono-substituted TSA precursor being (SiH$_3$)$_2$N—SiH$_2$—(OSiI$_3$);
the mono-substituted TSA precursor being (SiH$_3$)$_2$N—SiH$_2$—(OSiMe$_3$);
the Si-containing film forming composition comprising between approximately 95% w/w and approximately 100% w/w of the precursor;
the Si-containing film forming composition comprising between approximately 5% w/w and approximately 50% w/w of the precursor;
the Si-containing film forming composition comprising between approximately 0 ppbw and approximately 500 ppbw Al;
the Si-containing film forming composition comprising between approximately 0 ppbw and approximately 500 ppbw As;
the Si-containing film forming composition comprising between approximately 0 ppbw and approximately 500 ppbw Ba;
the Si-containing film forming composition comprising between approximately 0 ppbw and approximately 500 ppbw Be;
the Si-containing film forming composition comprising between approximately 0 ppbw and approximately 500 ppbw Bi;
the Si-containing film forming composition comprising between approximately 0 ppbw and approximately 500 ppbw Cd;
the Si-containing film forming composition comprising between approximately 0 ppbw and approximately 500 ppbw Ca;
the Si-containing film forming composition comprising between approximately 0 ppbw and approximately 500 ppbw Cr;
the Si-containing film forming composition comprising between approximately 0 ppbw and approximately 500 ppbw Co;
the Si-containing film forming composition comprising between approximately 0 ppbw and approximately 500 ppbw Cu;
the Si-containing film forming composition comprising between approximately 0 ppbw and approximately 500 ppbw Ga;
the Si-containing film forming composition comprising between approximately 0 ppbw and approximately 500 ppbw Ge;
the Si-containing film forming composition comprising between approximately 0 ppbw and approximately 500 ppbw Hf;
the Si-containing film forming composition comprising between approximately 0 ppbw and approximately 500 ppbw Zr;
the Si-containing film forming composition comprising between approximately 0 ppbw and approximately 500 ppbw In;
the Si-containing film forming composition comprising between approximately 0 ppbw and approximately 500 ppbw Fe;
the Si-containing film forming composition comprising between approximately 0 ppbw and approximately 500 ppbw Pb;
the Si-containing film forming composition comprising between approximately 0 ppbw and approximately 500 ppbw Li;
the Si-containing film forming composition comprising between approximately 0 ppbw and approximately 500 ppbw Mg;

the Si-containing film forming composition comprising between approximately 0 ppbw and approximately 500 ppbw Mn;
the Si-containing film forming composition comprising between approximately 0 ppbw and approximately 500 ppbw W;
the Si-containing film forming composition comprising between approximately 0 ppbw and approximately 500 ppbw Ni;
the Si-containing film forming composition comprising between approximately 0 ppbw and approximately 500 ppbw K;
the o Si-containing film forming composition comprising between approximately 0 ppbw and approximately 500 ppbw Na;
the Si-containing film forming composition comprising between approximately 0 ppbw and approximately 500 ppbw Sr;
the Si-containing film forming composition comprising between approximately 0 ppbw and approximately 500 ppbw Th;
the Si-containing film forming composition comprising between approximately 0 ppbw and approximately 500 ppbw Sn;
the Si-containing film forming composition comprising between approximately 0 ppbw and approximately 500 ppbw Ti;
the Si-containing film forming composition comprising between approximately 0 ppbw and approximately 500 ppbw U;
the Si-containing film forming composition comprising between approximately 0 ppbw and approximately 500 ppbw V;
the Si-containing film forming composition comprising between approximately 0 ppbw and approximately 500 ppbw Zn;
the Si-containing film forming organosilane composition comprising between approximately 0 ppmw and approximately 500 ppmw Cl;
the Si-containing film forming composition comprising between approximately 0 ppmw and approximately 500 ppmw Br;
the Si-containing film forming composition comprising between approximately 0 ppmw and approximately 500 ppmw I;
the Si-containing film forming composition comprising between approximately 0.0% w/w and 0.1% w/w TSA;
the Si-containing film forming composition comprising between approximately 0.0% w/w and 0.1% w/w $(SiH_3)_2$—N—$SiH_2X$, wherein X is Cl, Br, or I;
the Si-containing film forming composition comprising between approximately 0.0% w/w and 0.1% w/w $(SiH_3)_2$—N—$SiHX_2$, wherein X is Cl, Br, or I;
the Si-containing film forming composition comprising between approximately 0.0% w/w and 0.1% w/w $SiH_4$;
the Si-containing film forming composition comprising between approximately 0.0% w/w and 0.1% w/w $SiH_3X$, wherein X is Cl, Br, or I;
the Si-containing film forming composition comprising between approximately 0.0% w/w and 0.1% w/w $SiH_2X_2$, wherein X is Cl, Br, or I;
the Si-containing film forming composition comprising between approximately 0.0% w/w and 0.1% w/w $SnX_2$, wherein X is Cl, Br, or I;
the Si-containing film forming composition comprising between approximately 0.0% w/w and 0.1% w/w $SnX_4$, wherein X is Cl, Br, or I;
the Si-containing film forming composition comprising between approximately 0.0% w/w and 0.1% w/w HX, wherein X is Cl, Br, or I;
the Si-containing film forming composition comprising between approximately 0.0% w/w and 0.1% w/w $NH_3$;
the Si-containing film forming composition comprising between approximately 0.0% w/w and 0.1% w/w $NH_4X$, wherein X is Cl, Br, or I;
the Si-containing film forming composition comprising between approximately 0.0% w/w and 0.1% w/w ROH, wherein R is C1-C4 alkyl group;
the Si-containing film forming composition comprising between approximately 0.0% w/w and 0.1% w/w $NH_2R$, wherein R is a C1-C4 alkyl group;
the Si-containing film forming composition comprising between approximately 0.0% w/w and 0.1% w/w $NR_2H$, wherein R is a C1-C4 alkyl group;
the Si-containing film forming composition comprising between approximately 0.0% w/w and 0.1% w/w HN=R, wherein R is a C1-C4 alkyl group;
the Si-containing film forming composition comprising between approximately 0.0% w/w and 0.1% w/w tetrahydrofuran (THF);
the Si-containing film forming composition comprising between approximately 0.0% w/w and 0.1% w/w ether;
the Si-containing film forming composition comprising between approximately 0.0% w/w and 0.1% w/w pentane;
the Si-containing film forming composition comprising between approximately 0.0% w/w and 0.1% w/w cyclohexane;
the Si-containing film forming composition comprising between approximately 0.0% w/w and 0.1% w/w heptane; or
the Si-containing film forming composition comprising between approximately 0.0% w/w and 0.1% w/w toluene.

Also disclosed are methods of depositing a Si-containing layer on a substrate. The composition disclosed above is introduced into a reactor having a substrate disposed therein. At least part of the mono-substituted TSA precursor is deposited onto the substrate to form the Si-containing layer using a vapor deposition method. The disclosed methods may have one or more of the following aspects:

introducing into the reactor a vapor comprising a second precursor;

an element of the second precursor being selected from the group consisting of group 2, group 13, group 14, transition metal, lanthanides, and combinations thereof;

the element of the second precursor being selected from As, B, P, Si, Ge, Al, Zr, Hf, Ti, Nb, Ta, or lanthanides;

introducing a reactant into the reactor;

the reactant being selected from the group consisting of $O_2$, $O_3$, $H_2O$, $H_2O_2$, NO, $NO_2$, a carboxylic acid, an alcohol, a diol, radicals thereof, and combinations thereof;

the reactant being plasma treated oxygen;

the Si-containing layer being a silicon oxide containing layer;

the reactant being selected from the group consisting of $N_2$, $H_2$, $NH_3$, hydrazines (such as $N_2H_4$, $MeHNNH_2$, MeHNNHMe), organic amines (such as $NMeH_2$, $NEtH_2$, $NMe_2H$, $NEt_2H$, $NMe_3$, $NEt_3$, $(SiMe_3)_2NH$), pyrazoline, pyridine, diamines (such as ethylene diamine), radical species thereof, and mixtures thereof;

the vapor deposition method being a chemical vapor deposition process;

the vapor deposition method being an ALD process;
the vapor deposition method being a spatial ALD process;
the vapor deposition process being a flowable CVD process;
the silicon-containing layer being Si;
the silicon-containing layer being $SiO_2$;
the silicon-containing layer being SiN;
the silicon-containing layer being SiON;
the silicon-containing layer being SiOC;
the silicon-containing layer being SiOCN;
the silicon-containing layer being SiCN;
thermal annealing the Si-containing layer;
thermal annealing the Si-containing layer under a reactive atmosphere;
UV curing the Si-containing layer; and
Electron beam curing the Si-containing layer.

Also disclosed are nitrogen-doped silicon oxide films formed by the process of introducing into a reactor containing a substrate a vapor including a mono-substituted TSA precursor to form a silicon-containing layer on the substrate; reacting an oxidizing agent with the silicon-containing layer to form an oxidized silicon-containing layer by introducing the oxidizing agent into the reactor; reacting the mono-substituted TSA precursor with the oxidized silicon-containing layer to form a silicon-rich oxidized silicon-containing layer by introducing the mono-substituted TSA precursor into the reactor; and reacting a nitrogen-containing reactant with the silicon-containing layer to form the nitrogen-doped silicon oxide film by introducing the nitrogen-containing reactant into the reactor. The mono-substituted TSA precursors have a formula $(SiH_3)_2N$—$SiH_2$—X, wherein X is selected from a halogen atom selected from Cl, Br or I; an isocyanato group [—NCO]; an amino group [—$NR^1R^2$]; a N-containing $C_4$-$C_{10}$ saturated or unsaturated heterocycle; or an alkoxy group [—O—R]; $R^1$, $R^2$ and R each is selected from H; a $C_1$-$C_6$ linear or branched, saturated or unsaturated hydrocarbyl group; or a silyl group $SiR'_3$ with each R' being independently selected from H; a halogen atom selected from Cl, Br, or I; a $C_1$-$C_4$ saturated or unsaturated hydrocarbyl group; a $C_1$-$C_4$ saturated or unsaturated alkoxy group; or an amino group —$NR^3R^4$ with each $R^3$ and $R^4$ being selected from H or a $C_1$-$C_6$ linear or branched, saturated or unsaturated hydrocarbyl group, provided that if $R^1$=H, then $R^2 \neq$ H or Me. The process to produce the disclosed nitrogen-doped silicon oxide films may include one or more of the following aspects:

purging the reactor with an inert gas between each introduction step;
the mono-substituted TSA precursor wherein X is a halogen atom;
the mono-substituted TSA precursor being $(SiH_3)_2N$—$SiH_2$—Cl;
the mono-substituted TSA precursor being $(SiH_3)_2N$—$SiH_2$—Br;
the mono-substituted TSA precursor being $(SiH_3)_2N$—$SiH_2$—I;
the mono-substituted TSA precursor wherein X is a isocyanate —NCO (i.e., being $(SiH_3)_2N$—$SiH_2$—NCO);
the mono-substituted TSA precursor wherein X is an amino group [—$NR^1R^2$];
the mono-substituted TSA precursor being $(SiH_3)_2N$—$SiH_2$—$NiPr_2$;
the mono-substituted TSA precursor being $(SiH_3)_2N$—$SiH_2$—NHiPr;
the mono-substituted TSA precursor being $(SiH_3)_2N$—$SiH_2$—NHtBu;
the mono-substituted TSA precursor not being $(SiH_3)_2$—N—$SiH_2$—$N(SiH_3)(SiH_2(NHEt))$ (i.e., when X=$NR^1R^2$ and $R^1$ is $SiH_3$ and $R^2$ is NHEt);
the mono-substituted TSA precursor being $(SiH_3)_2N$—$SiH_2$—$NEt_2$;
the mono-substituted TSA precursor being $(SiH_3)_2N$—$SiH_2NEtMe$;
the mono-substituted TSA precursor being $(SiH_3)_2N$—$SiH_2NMe_2$;
the mono-substituted TSA precursor being $(SiH_3)_2N$—$SiH_2NMeiPr$;
the mono-substituted TSA precursor being $(SiH_3)_2N$—$SiH_2NEtiPr$;
the mono-substituted TSA precursor wherein X is —$N(SiR_3)_2$, wherein each R is independently selected from a halogen, H, or a $C_1$-$C_4$ alkyl group;
the mono-substituted TSA precursor being $(SiH_3)_2N$—$SiH_2$—$N(SiCl_3)_2$;
the mono-substituted TSA precursor being $(SiH_3)_2N$—$SiH_2$—$N(SiBr_3)_2$;
the mono-substituted TSA precursor being $(SiH_3)_2N$—$SiH_2$—$N(SiI_3)_2$;
the mono-substituted TSA precursor being $(SiH_3)_2N$—$SiH_2$—$N(SiH_3)_2$;
the mono-substituted TSA precursor being $(SiH_3)_2$—N—$SiH_2$—$N(SiH_3)(SiH_2Cl)$;
the mono-substituted TSA precursor being $(SiH_3)_2$—N—$SiH_2$—$N(SiH_3)(SiH_2(NEt_2)$;
the mono-substituted TSA precursor being $(SiH_3)_2$—N—$SiH_2$—$N(SiH_3)(SiH_2(NiPr_2)$;
the mono-substituted TSA precursor being $(SiH_3)_2$—N—$SiH_2$—$N(SiH_3)(SiH_2(NHtBu)$;
the mono-substituted TSA precursor being $(SiH_3)_2$—N—$SiH_2$—$N(SiH_3)(SiH_2OEt)$;
the mono-substituted TSA precursor being $(SiH_3)_2$—N—$SiH_2$—$N(SiH_3)(SiH_2OiPr)$;
the mono-substituted TSA precursor being $(SiH_3)_2N$—$SiH_2$—$N(SiMe_3)_2$;
the mono-substituted TSA precursor being $(SiH_3)_2N$—$SiH_2$—$NH(SiMe_3)$;
the mono-substituted TSA precursor being $(SiH_3)_2N$—$SiH_2$—$N(SiEt_3)_2$;
the mono-substituted TSA precursor being $(SiH_3)_2N$—$SiH_2$—$N(SiMe_2Et)_2$;
the mono-substituted TSA precursor being $(SiH_3)_2N$—$SiH_2$—$N(SiMe_2iPr)_2$;
the mono-substituted TSA precursor being $(SiH_3)_2N$—$SiH_2$—$N(SiMe_2nPr)_2$;
the mono-substituted TSA precursor wherein X is a N-containing $C_4$-$C_{10}$ heterocycle;
the mono-substituted TSA precursor wherein the N-containing $C_4$-$C_{10}$ heterocycle is selected from pyrrolidine, pyrrole, and piperidine;
the mono-substituted TSA precursor being $(SiH_3)_2N$—$SiH_2$-(pyrrolidine);
the mono-substituted TSA precursor being $(SiH_3)_2N$—$SiH_2$-(pyrrole);
the mono-substituted TSA precursor being $(SiH_3)_2N$—$SiH_2$-(piperidine);
the mono-substituted TSA precursor wherein X is an alkoxy group [—O—R];
the mono-substituted TSA precursor being $(SiH_3)_2N$—$SiH_2$—(OH);
the mono-substituted TSA precursor being $(SiH_3)_2N$—$SiH_2$—(OMe);
the mono-substituted TSA precursor being $(SiH_3)_2N$—$SiH_2$—(OEt);

the mono-substituted TSA precursor being (SiH$_3$)$_2$N—SiH$_2$—(OiPr);

the mono-substituted TSA precursor being (SiH$_3$)$_2$N—SiH$_2$—(OnPr);

the mono-substituted TSA precursor being (SiH$_3$)$_2$N—SiH$_2$—(OtBu);

the mono-substituted TSA precursor wherein X is —O—SiR$_3$ and each R is independently selected from H, a halogen, or a C$_1$-C$_4$ hydrocarbyl group;

the mono-substituted TSA precursor being (SiH$_3$)$_2$N—SiH$_2$—(OSiH$_3$);

the mono-substituted TSA precursor being (SiH$_3$)$_2$N—SiH$_2$—(OSiCl$_3$);

the mono-substituted TSA precursor being (SiH$_3$)$_2$N—SiH$_2$—(OSiBr$_3$);

the mono-substituted TSA precursor being (SiH$_3$)$_2$N—SiH$_2$—(OSiI$_3$);

the mono-substituted TSA precursor being (SiH$_3$)$_2$N—SiH$_2$—(OSiMe$_3$);

the reactant being selected from the group consisting of O$_2$, O$_3$, H$_2$O, H$_2$O$_2$, NO, NO$_2$, a carboxylic acid, an alcohol, a diol, radicals thereof, and combinations thereof; and the reactant being selected from the group consisting of N$_2$, H$_2$, NH$_3$, hydrazines (such as N$_2$H$_4$, MeHNNH$_2$, MeHNNHMe), organic amines (such as NMeH$_2$, NEtH$_2$, NMe$_2$H, NEt$_2$H, NMe$_3$, NEt$_3$, (SiMe$_3$)$_2$NH), pyrazoline, pyridine, diamines (such as ethylene diamine), radical species thereof, and mixtures thereof.

Notation and Nomenclature

The following detailed description and claims utilize a number of abbreviations, symbols, and terms, which are generally well known in the art. While definitions are typically provided with the first instance of each acronym, for convenience, Table 1 provides a list of the abbreviations, symbols, and terms used along with their respective definitions.

TABLE 1

| | |
|---|---|
| a or an | One or more than one |
| Approximately or about | ±10% of the value stated |
| LCD-TFT | liquid-crystal display-thin-film transistor |
| MIM | Metal-insulator-metal |
| DRAM | dynamic random-access memory |
| FeRam | Ferroelectric random-access memory |
| OLED | organic light-emitting diode |
| CVD | chemical vapor deposition |
| LPCVD | low pressure chemical vapor deposition |
| PCVD | pulsed chemical vapor deposition |
| SACVD | sub-atmospheric chemical vapor deposition |
| PECVD | plasma enhanced chemical vapor deposition |
| APCVD | atmospheric pressure chemical vapor deposition |
| HWCVD | hot-wire chemical vapor deposition |
| FCVD | flowable chemical vapor deposition |
| MOCVD | metal organic chemical vapor deposition |
| ALD | atomic layer deposition |
| spatial ALD | spatial atomic layer deposition |
| HWALD | hot-wire atomic layer deposition |
| PEALD | plasma enhanced atomic layer deposition |
| sccm | standard cubic centimeters per minute |
| MP | melting point |
| TGA | thermogravimetric analysis |
| SDTA | simultaneous differential thermal analysis |
| GCMS | gas chromatography-mass spectrometry |
| TSA | trisilylamine |
| SRO | strontium ruthenium oxide |
| HCDS | hexachlorodisilane |
| PCDS | pentachlorodisilane |

TABLE 1-continued

| | |
|---|---|
| OCTS | n-octyltrimethoxysilane |
| MCS | monochlorosilane |
| DCS | dichlorosilane |
| TSA | Trisilylamine |
| DSA | disilylamine |
| TriDMAS or TDMAS | tris(dimethylamino)silane or SiH(NMe$_2$)$_3$ |
| BDMAS | bis(dimethylamino)silane or SiH$_2$(NMe$_2$)$_2$ |
| BDEAS | bis(diethylamino)silane or SiH$_2$(NEt$_2$)$_2$ |
| TDEAS | tris(diethylamino)silane or SiH(NEt$_2$)$_3$ |
| TEMAS | tris(ethylmethylamino)silane or SiH(N EtMe)$_3$ |
| TMA | trimethyl aluminum or AlMe$_3$ |
| PET | polyethylene terephthalate |
| TBTDEN | (tert-butylimido)bis(dimethylamino)niobium or Nb(=NtBu)(NMe$_2$)$_2$ |
| PEN | polyethylene naphthalate |
| PEDOT:PSS | poly(3,4-ethylenedioxythiophene)poly(styrenesulfonate) |
| Alkyl group | saturated functional groups containing exclusively carbon and hydrogen atoms, including linear, branched, or cyclic alkyl groups |
| Me | Methyl |
| Et | Ethyl |
| iPr | isopropyl |
| aryl | aromatic ring compounds where one hydrogen atom has been removed from the ring |
| heterocycle | cyclic compounds that has atoms of at least two different elements as members of its ring |
| PTFE | Polytetrafluoroethylene |

The standard abbreviations of the elements from the periodic table of elements are used herein. It should be understood that elements may be referred to by these abbreviations (e.g., Si refers to silicon, N refers to nitrogen, O refers to oxygen, C refers to carbon, etc.).

As used herein, the term "independently" when used in the context of describing R groups should be understood to denote that the subject R group is not only independently selected relative to other R groups bearing the same or different subscripts or superscripts, but is also independently selected relative to any additional species of that same R group. For example in the formula MR$^1_x$ (NR$^2$R$^3$)$_{(4-x)}$, where x is 2 or 3, the two or three R$^1$ groups may, but need not be identical to each other or to R$^2$ or to R$^3$. Further, it should be understood that unless specifically stated otherwise, values of R groups are independent of each other when used in different formulas.

BRIEF DESCRIPTION OF THE FIGURES

For a further understanding of the nature and objects of the present invention, reference should be made to the following detailed description, taken in conjunction with the accompanying figure wherein.

DESCRIPTION OF PREFERRED EMBODIMENTS

Figure 1:
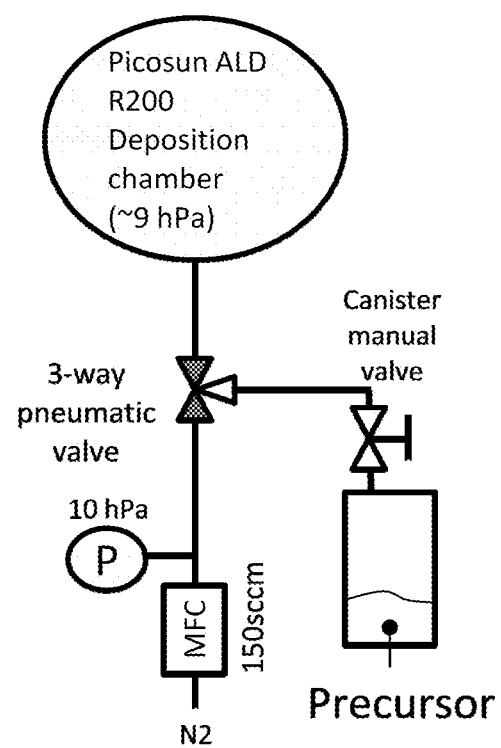
FIG. 1 is a diagram of the Picosun R200 PEALD 8" deposition tool used to perform the depositions in Examples 4-6.

Disclosed are Si-containing film forming compositions comprising mono-substituted TSA precursors having a Si—C bond free backbone and a single chemically functionalized site to enable a high surface reactivity. Monosubstituted TSA precursors having a number of silicon atoms higher than 1, and preferably higher than 2, without a direct Si—C bond, and being polar molecules may have an enhanced reactivity to a substrate surface to enable a fast deposition rate. The mono-substituted TSA precursors have the general formula:

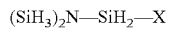

$(SiH_3)_2N—SiH_2—X$ wherein X is selected from a halogen atom selected from Cl, Br or I; an isocyanato group [—NCO]; an amino group [—NR$^1$R$^2$]; a N-containing $C_4$-$C_{10}$ saturated or unsaturated heterocycle; or an alkoxy group —O—R; each R$^1$, R$^2$ and R selected from a H; a silyl group (SiR'$_3$); or a $C_1$-$C_6$ linear or branched, saturated or unsaturated hydrocarbyl group; with each R' being independently selected from H; a halogen atom selected from Cl, Br, or I; a $C_1$-$C_4$ saturated or unsaturated hydrocarbyl group; a $C_1$-$C_4$ saturated or unsaturated alkoxy group; or an amino group [—NR$^3$R$^4$], with each R$^3$ and R$^4$ being independently selected from H or a $C_1$-$C_6$ linear or branched, saturated or unsaturated hydrocarbyl group; provided that if R$^1$=H, then R$^2$≠H, Me, or Et. The $C_1$-$C_6$ linear or branched, saturated or unsaturated hydrocarbyl group may contain amines or ethers. Alternatively, R$^1$ and R$^2$ may be independently selected from Me, Et, iPr, nPr, tBu, nBu, and secBu.

When X is a halide, exemplary Si-containing film forming compositions include $(SiH_3)_2$—N—SiH$_2$Cl, $(SiH_3)_2$—N—SiH$_2$Br, or $(SiH_3)_2$—N—SiH$_2$I. These compositions may be synthesized according to the reaction: SnX$_4$+N(SiH$_3$)$_3$→N(SiH$_3$)$_2$(SiH$_2$X)+SnX$_2$↓+HXI, wherein X is Cl, Br, or I (see *J. Chem. Soc. Dalton Trans.* 1975, p. 1624). Alternatively, dihalosilane [SiH$_2$X$_2$, wherein X is Cl, Br, or I] and monohalosilane [SiH$_3$X, wherein X is Cl, Br, or I] may be introduced continuously in the gas phase in a ½₀ to ¼ ratio and at room temperature with 400 sccm of NH$_3$ in a flow-through tubular reactor as described by Miller in U.S. Pat. No. 8,669,387. The reaction of NH$_3$ with 2 equivalents of monohalosilane produces mostly disilylamine (DSA). DSA then reacts with the dihalosilane to form $(SiH_3)_2$—N—SiH$_2$X and HX, wherein X is Cl, Br, or I. One of ordinary skill in the art would recognize that the reaction may take place in one or two steps (first forming DSA from the monohalosilane and NH$_3$ and second adding dihalosilane) or in one step (combining the monohalosilane, dichlorosilane, and NH$_3$ in one step).

When X is an isocyanato group [—NCO], exemplary Si-containing film forming compositions include $(SiH_3)_2$—N—SiH$_2$(NCO). This composition may be synthesized using dehydrogenerative coupling according to the method disclosed by Taniguchi et al. in Angewandte Communications, Angew. Chem. Int. Ed. 2013, 52, 1-5, the teachings of which are incorporated herein by reference. More particularly, $(SiH_3)_3$N may be reacted with urea (NH$_2$CONH$_2$) to form $(SiH_3)_2$—N—SiH$_2$(NCO)+H$_2$ in the presence of gold nanoparticles supported on alumina.

When X is an amino group [—NR$^1$R$^2$], exemplary Si-containing film forming compositions include $(SiH_3)_2$—N—SiH$_2$(NEt$_2$), $(SiH_3)_2$—N—SiH$_2$(NiPr$_2$), $(SiH_3)_2$—N—SiH$_2$(NHiPr), $(SiH_3)_2$—N—SiH$_2$(NHtBu), $(SiH_3)_2$—N—SiH$_2$[N(SiH$_3$)$_2$], $(SiH_3)_2$—N—SiH$_2$[N(SiH$_3$)(SiH$_2$Cl)], $(SiH_3)_2$—N—SiH$_2$[N(SiH$_3$)(SiH$_2$(NEt$_2$))], $(SiH_3)_2$—N—SiH$_2$[N(SiH$_3$)(SiH$_2$(NiPr$_2$))], $(SiH_3)_2$—N—SiH$_2$[N(SiH$_3$)(SiH$_2$(NHtBu))], $(SiH_3)_2$—N—SiH$_2$[N(SiH$_3$)(SiH$_2$OEt)], $(SiH_3)_2$—N—SiH$_2$[N(SiH$_3$)(SiH$_2$OiPr)], $(SiH_3)_2$—N—SiH$_2$[N(SiMe$_3$)$_2$], $(SiH_3)_2$—N—SiH$_2$[NH(SiMe$_3$)], $(SiH_3)_2$—N—SiH$_2$[N(SiEt$_3$)$_2$], $(SiH_3)_2$—N—SiH$_2$[N(SiMe$_2$Et)$_2$], $(SiH_3)_2$—N—SiH$_2$[N(SiMe$_3$iPr)$_2$], $(SiH_3)_2$—N—SiH$_2$[N(tBu)(SiH$_3$)), $(SiH_3)_2$—N—SiH$_2$[N(SiMe$_2$nPr)$_2$), $(SiH_3)_2$N—SiH$_2$NEtMe, $(SiH_3)_2$N—SiH$_2$NMe$_2$, $(SiH_3)_2$N—SiH$_2$NMeiPr, or $(SiH_3)_2$N—SiH$_2$NEtiPr.

The amino-substituted Si-containing film forming compositions may be synthesized similarly to the halo-substituted Si-containing film forming compositions disclosed above. More particularly, 200 sccm of monohalosilane and 50 sccm of dihalosilane may be introduced continuously in the gas phase and at room temperature with 400 sccm of NH$_3$ in a flow-through tubular reactor as described in U.S. Pat. No. 8,669,387, forming a stream consisting of various silylamines and ammonium halide, from which $(SiH_3)_2$—N—SiH$_2$[N(SiH$_3$)$_2$] may be isolated by methods easily derived by a person having ordinary skill in the art, such as a method of fractional distillation.

More particularly, $(SiH_3)_2$—N—SiH$_2$[N(SiMe$_3$)$_2$] may be synthesized from the reaction of SiMe$_3$-NH—SiMe$_3$ with tBuLi→(Me$_3$Si)$_2$NLi, and reaction of (Me$_3$Si)$_2$NLi with $(SiH_3)_2$—N—SiH$_2$—Cl→$(SiH_3)_2$—N—SiH$_2$—N(SiMe$_3$)$_2$+LiCl).

Similarly, $(SiH_3)_2$—N—SiH$_2$—NH(SiMe$_3$) may be synthesized from the reaction of SiMe$_3$-NH—SiMe$_3$+$(SiH_3)_2$—N—SiH$_2$—Cl→$(SiH_3)_2$—N—SiH$_2$—NH—SiMe$_3$+Me$_3$SiCl.

$(SiH_3)_2$—N—SiH$_2$—N(SiH$_3$)(SiH$_2$X) may be synthesized from the reaction of $(SiH_3)_2$—N—SiH$_2$—N(SiH$_3$)$_2$ with SnX$_3$, wherein X is Cl, Br, or I (see *J. Chem. Soc. Dalton Trans.* 1975, p. 1624). Further substitution of $(SiH_3)_2$—N—SiH$_2$—N(SiH$_3$)$_2$ may be achieved by increasing the reaction time and/or adjusting the stoichiometry.

$(SiH_3)_2$—N—SiH$_2$—N(SiH$_3$)(SiH$_2$(NEt$_2$)) may be synthesized from the reaction of $(SiH_3)_2$—N—SiH$_2$—N(SiH$_3$)(SiH$_2$X) and HNEt$_2$. Further substitution of $(SiH_3)_2$—N—SiH$_2$—N(SiH$_3$)(SiH$_2$(NEt$_2$)) may be achieved by increasing the reaction time and/or adjusting the stoichiometry.

$(SiH_3)_2$—N—SiH$_2$—N(SiH$_3$)(SiH$_2$(NiPr$_2$)) may be synthesized from the reaction of $(SiH_3)_2$—N—SiH$_2$—N(SiH$_3$)(SiH$_2$X) and HNiPr$_2$. Further substitution of $(SiH_3)_2$—N—SiH$_2$—N(SiH$_3$)(SiH$_2$(NiPr$_2$)) may be achieved by increasing the reaction time and/or adjusting the stoichiometry.

$(SiH_3)_2$—N—SiH$_2$—N(SiH$_3$)(SiH$_2$(NHtBu)) may be synthesized from the reaction of $(SiH_3)_2$—N—SiH$_2$—N(SiH$_3$)(SiH$_2$X) and H$_2$NtBu. Please note that a similar reaction using H$_2$NEt may produce low yields of $(SiH_3)_2$—N—SiH$_2$—N(SiH$_3$)(SiH$_2$(NHEt)).

$(SiH_3)_2$—N—SiH$_2$—N(SiH$_3$)(SiH$_2$(OEt)) may be synthesized from the reaction of $(SiH_3)_2$—N—SiH$_2$—N(SiH$_3$)(SiH$_2$X) and Ethanol (EtOH) in the presence of a HCl scavenger, like NEt$_3$ or pyridine.

$(SiH_3)_2$—N—SiH$_2$—N(SiH$_3$)(SiH$_2$(OiPr)) may be synthesized from the reaction of $(SiH_3)_2$—N—SiH$_2$—N(SiH$_3$)(SiH$_2$X) and isopropanol (iPrOH) in the presence of a HCl scavenger, like NEt$_3$ or pyridine.

When X is a N-containing $C_4$-$C_{10}$ saturated or unsaturated heterocycle, exemplary Si-containing film forming compositions include $(SiH_3)_2$—N—SiH$_2$-pyrrolidine, $(SiH_3)_2$—N—SiH$_2$-pyrrole, or $(SiH_3)_2$—N—SiH$_2$-piperidine. Alternatively, the N-containing $C_4$-$C_{10}$ saturated or unsaturated heterocycle may also contain hetero-elements, such as P, B, As, Ge, and/or Si.

When X is an alkoxy group, exemplary Si-containing film forming compositions include $(SiH_3)_2$—N—SiH$_2$(OEt), $(SiH_3)_2$—N—$SiH_2$(OiPr), $(SiH_3)_2$N—$SiH_2$—$OSiMe_3$, $(SiH_3)_2$—N—$SiH_2$—$OSiMe_2OEt$, or $(SiH_3)_2$—N—$SiH_2$—$OSiHMe_2$.

$N(SiH_3)_2(SiH_2OEt)$ may also be synthesized from $(SiH_3)_2$—N—$SiH_2Cl$ and EtOH in the presence of an acid scavenger, such as $Et_3N$ or pyridine.

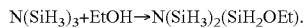

$N(SiH_3)_3 + EtOH \rightarrow N(SiH_3)_2(SiH_2OEt)$.

Preferably, the disclosed Si-containing film forming compositions have suitable properties for vapor depositions methods, such as high vapor pressure, low melting point (preferably being in liquid form at room temperature), low sublimation point, and/or high thermal stability.

To ensure process reliability, the disclosed Si-containing film forming compositions may be purified by continuous or fractional batch distillation prior to use to a purity ranging from approximately 95% w/w to approximately 100% w/w, preferably ranging from approximately 98% w/w to approximately 100% w/w. One of ordinary skill in the art will recognize that the purity may be determined by H NMR or gas or liquid chromatography with mass spectrometry. The Si-containing film forming composition may contain any of the following impurities: halides ($X_2$), trisilylamine, mono-halotrisilylamine, dihalotrisilylamine, $SiH_4$, $SiH_3X$, $SnX_2$, $SnX_4$, HX, $NH_3$, $NH_3X$, monochlorosilane, dichlorosilane, alcohol, alkylamines, dialkylamines, alkylimines, THF, ether, pentane, cyclohexane, heptanes, or toluene, wherein X is Cl, Br, or I. Preferably, the total quantity of these impurities is below 0.1% w/w. The purified composition may be produced by recrystallisation, sublimation, distillation, and/or passing the gas or liquid through a suitable adsorbent, such as a 4 A molecular sieve or a carbon-based adsorbent (e.g., activated carbon).

The concentration of each solvent (such as THF, ether, pentane, cyclohexane, heptanes, and/or toluene), in the purified mono-substituted TSA precursor composition may range from approximately 0% w/w to approximately 5% w/w, preferably from approximately 0% w/w to approximately 0.1% w/w. Solvents may be used in the precursor composition's synthesis. Separation of the solvents from the precursor composition may be difficult if both have similar boiling points. Cooling the mixture may produce solid precursor in liquid solvent, which may be separated by filtration. Vacuum distillation may also be used, provided the precursor composition is not heated above approximately its decomposition point.

The disclosed Si-containing film forming composition contains less than 5% v/v, preferably less than 1% v/v, more preferably less than 0.1% v/v, and even more preferably less than 0.01% v/v of any of its mono-, dual- or tris-, analogs or other reaction products. This embodiment may provide better process repeatability. This embodiment may be produced by distillation of the Si-containing film forming composition.

Purification of the disclosed Si-Containing film forming composition may also produce concentrations of trace metals and metalloids ranging from approximately 0 ppbw to approximately 500 ppbw, and more preferably from approximately 0 ppbw to approximately 100 ppbw. These metal or metalloid impurities include, but are not limited to, Aluminum(Al), Arsenic(As), Barium(Ba), Beryllium(Be), Bismuth(Bi), Cadmium(Cd), Calcium(Ca), Chromium(Cr), Cobalt(Co), Copper(Cu), Gallium(Ga), Germanium(Ge), Hafnium(Hf), Zirconium(Zr), Indium(In), Iron(Fe), Lead (Pb), Lithium(Li), Magnesium(Mg), Manganese(Mn), Tungsten(W), Nickel(Ni), Potassium(K), Sodium(Na), Strontium(Sr), Thorium(Th), Tin(Sn), Titanium(Ti), Uranium(U), Vanadium(V) and Zinc(Zn). The concentration of X (where X=Cl, Br, I) in the purified mono-substituted TSA precursor composition may range between approximately 0 ppmw and approximately 100 ppmw and more preferably between approximately 0 ppmw to approximately 10 ppmw.

The disclosed Si-containing film forming compositions may be suitable for the deposition of Si-containing films by various ALD or CVD processes and may have the following advantages:
  liquid at room temperature or having a melting point lower than 50° C.;
  thermally stable to enable proper distribution (gas phase or direct liquid injection) without particles generation; and/or
  suitable reactivity with the substrate to permit a wide self-limited ALD window, allowing deposition of a variety of Si-containing films.

Silicon nitride and silicon oxide containing films (referred to as $SiO_xN_y$) may be deposited by CVD or ALD using one or a combination of reactants selected from the group comprising of $N_2$, $H_2$, $NH_3$, $O_2$, $H_2O$, $H_2O_2$, $O_3$, NO, $NO_2$, $N_2O$, a carboxylic acid, an alcohol, a diol, hydrazines (such as $N_2H_4$, $MeHNNH_2$, $MeHNNHMe$), organic amines (such as $NMeH_2$, $NEtH_2$, $NMe_2H$, $NEt_2H$, $NMe_3$, $NEt_3$, $(SiMe_3)_2$ NH), pyrazoline, pyridine, diamines (such as ethylene diamine), a combination thereof, and the plasma product thereof.

Ternary or quarternary films may be deposited using the Si-containing film forming compositions with one or several other precursors containing elements selected from As, B, P, Ga, Ge, Sn, Sb, Al, In, or a transition metal precursor, and possibly one or more reactant listed above. Typical precursors that may be used along with the disclosed Si-containing film forming compositions are selected from the families of:
  Metal Halides (for example, $TiCl_4$, $TiI_4$, $TaCl_5$, $HfCl_4$, $ZrCl_4$, $AlCl_3$, $NbF_5$, etc.);
  Alkyls (Al, Ge, Ga, In, Sb, Sn, Zn), such as trimethylaluminum, diethylzinc, triethylgalium;
  Hydrides ($GeH_4$, alanes, etc.);
  Alkylamides (metals of group IV and V transition metals);
  Imido group (metals of group V and VI);
  Alkoxides (metals of group IV, V);
  Cyclopentadienyls (Ru, Co, Fe, Group IV transition metals, lanthanides etc.);
  Carbonyls (ex: Ru, Co, Fe, Ni);
  Amidinates and guanidinates (ex: Co, Mn, Ni, Cu, Sc, etc.);
  Beta-diketonates (ex: Sc, Cu, lanthanides);
  Beta-diketoimines (Cu, Ni, Co, etc.);
  Bis-trialkylsilylamides (Ni, Co, Fe, etc.);
  Oxo groups ($RuO_4$, $WOCl_4$, $PO(OEt)_3$, $AsO(OEt)_3$, etc.);
  Or heteroleptic molecules having a combination of the above ligands.

The disclosed Si-containing film forming compositions may also be used in conjunction with another silicon source, such as a halosilane (possibly selected from $SiH_3Cl$, $SiH_2Cl_2$, $SiHCl_3$, $SiCl_4$, $SiBr_4$, $SiI_4$, $SiHI_3$, $SiH_2I_2$, $SiH_3I$, $SiF_4$), a polysilane $SiH_xH_{2x+2}$, or a cyclic polysilane $SiH_xH_{2x}$, a halo-polysilane ($Si_xCl_{2x+2}$, $Si_xH_yCl_{2x+2-y}$, such as HCDS, OCTS, PCDS, MCDS or DCDS, a carbosilane having a Si—$(CH_2)_n$—Si backbone, with n=1 or 2.

Also disclosed are methods of using the disclosed Si-containing film forming compositions for vapor deposition methods, including various CVD and ALD methods. The disclosed methods provide for the use of the disclosed Si-containing film forming compositions for deposition of silicon-containing films, preferably silicon nitride (SiN) films, silicon-oxide (SiO) films, and nitrogen doped silicon-oxide films. The disclosed methods may be useful in the manufacture of semiconductor, photovoltaic, LCD-TFT, flat panel type devices, refractory materials, or aeronautics.

The disclosed methods for forming a silicon-containing layer on a substrate include: placing a substrate in a reactor, delivering into the reactor a vapor including the Si-containing film forming composition, and contacting the vapor with the substrate (and typically directing the vapor to the substrate) to form a silicon-containing layer on the surface of the substrate. Alternatively, the substrate is moved to the chamber that contains the precursor vapors (spatial ALD) and then moved to another area that contains the reactant. Other physical treatment steps may be carried in between the exposure to precursor and reactants, such as a flash anneal, a UV cure, etc.

The methods may include forming a bimetal-containing layer on a substrate using the vapor deposition process and, more specifically, for deposition of $SiMO_x$ films wherein x is 4 and M is Ti, Hf, Zr, Ta, Nb, V, Al, Sr, Y, Ba, Ca, As, B, P, Sb, Bi, Sn, lanthanides (such as Er), or combinations thereof. The disclosed methods may be useful in the manufacture of semiconductor, photovoltaic, LCD-TFT, or flat panel type devices. An oxygen source, such as $O_3$, $O_2$, $H_2O$, NO, $H_2O_2$, acetic acid, formalin, para-formaldehyde, alcohol, a diol, oxygen radicals thereof, and combinations thereof, but preferably $O_3$ or plasma treated $O_2$, may also be introduced into the reactor.

The disclosed Si-containing film forming compositions may be used to deposit silicon-containing films using any deposition methods known to those of skill in the art. Examples of suitable deposition methods include chemical vapor deposition (CVD) or atomic layer deposition (ALD). Exemplary CVD methods include thermal CVD, pulsed CVD (PCVD), low pressure CVD (LPCVD), subatmospheric CVD (SACVD) or atmospheric pressure CVD (APCVD), hot-wire CVD (HWCVD, also known as cat-CVD, in which a hot wire serves as an energy source for the deposition process), radicals incorporated CVD, plasma enhanced CVD (PECVD) including but not limited to flowable CVD (FCVD), and combinations thereof. Exemplary ALD methods include thermal ALD, plasma enhanced ALD (PEALD), spatial isolation ALD, hot-wire ALD (HWALD), radicals incorporated ALD, and combinations thereof. Super critical fluid deposition may also be used. The deposition method is preferably FCVD, ALD, PE-ALD, or spatial ALD in order to provide suitable step coverage and film thickness control.

The Si-containing film forming compositions are delivered into a reactor in vapor form by conventional means, such as tubing and/or flow meters. The vapor form of the compositions may be produced by vaporizing the neat or blended composition solution through a conventional vaporization step such as direct vaporization, distillation, by bubbling. The composition may be fed in liquid state to a vaporizer where it is vaporized before it is introduced into the reactor. Prior to vaporization, the composition may optionally be mixed with one or more solvents. The solvents may be selected from the group consisting of toluene, ethyl benzene, xylene, mesitylene, decane, dodecane, octane, hexane, pentane, or others. The resulting concentration may range from approximately 0.05 M to approximately 2 M.

Alternatively, the Si-containing film forming compositions may be vaporized by passing a carrier gas into a container containing the precursor or by bubbling of the carrier gas into the precursor. The composition may optionally be mixed in the container with one or more solvents. The solvents may be selected from the group consisting of toluene, ethyl benzene, xylene, mesitylene, decane, dodecane, octane, hexane, pentane, or others. The resulting concentration may range from approximately 0.05 M to approximately 2 M. The carrier gas may include, but is not limited to, Ar, He, or $N_2$, and mixtures thereof. Bubbling with a carrier gas may also remove any dissolved oxygen present in the neat or blended composition. The carrier gas and composition are then introduced into the reactor as a vapor.

If necessary, the container may be heated to a temperature that permits the Si-containing film forming composition to be in liquid phase and to have a sufficient vapor pressure. The container may be maintained at temperatures in the range of, for example, 0 to 150° C. Those skilled in the art recognize that the temperature of the container may be adjusted in a known manner to control the amount of composition vaporized. The temperature is typically adjusted to reach a vapor pressure of 0.1-100 torr, preferably around 1-20 torr.

The vapor of the Si-containing film forming composition is generated and then introduced into a reaction chamber containing a substrate. The temperature and the pressure in the reaction chamber and the temperature of the substrate are held at conditions suitable for vapor deposition of at least part of the mono-substituted TSA precursor onto the substrate. In other words, after introduction of the vaporized composition into the reaction chamber, conditions within the reaction chamber are adjusted such that at least part of the vaporized precursor is deposited onto the substrate to form the Si-containing layer. One of ordinary skill in the art will recognize that "at least part of the vaporized compound is deposited" means that some or all of the compound reacts with or adheres to the substrate. Herein, a reactant may also be used to help in formation of the Si-containing layer. Furthermore, the Si-containing layer may be cured by UV and Electron beam.

The reaction chamber may be any enclosure or chamber of a device in which deposition methods take place, such as, without limitation, a parallel-plate type reactor, a cold-wall type reactor, a hot-wall type reactor, a single-wafer reactor, a multi-wafer reactor, or other such types of deposition systems. All of these exemplary reaction chambers are capable of serving as an ALD or CVD reaction chamber. The reaction chamber may be maintained at a pressure ranging from about 0.5 mTorr to about 20 Torr for all ALD and subatmospheric CVD. Subatmospheric CVD and atmospheric CVD pressures may range up to 760 Torr (atmosphere). In addition, the temperature within the reaction chamber may range from about 0° C. to about 800° C. One of ordinary skill in the art will recognize that the temperature may be optimized through mere experimentation to achieve the desired result.

The temperature of the reactor may be controlled by either controlling the temperature of the substrate holder or controlling the temperature of the reactor wall. Devices used to heat the substrate are known in the art. The reactor wall is heated to a sufficient temperature to obtain the desired film at a sufficient growth rate and with desired physical state and composition. A non-limiting exemplary temperature range to which the reactor wall may be kept from approximately 20° C. to approximately 800° C. When a plasma deposition process is utilized, the deposition temperature may range from approximately 0° C. to approximately 550° C. Alternatively, when a thermal process is performed, the deposition temperature may range from approximately 200° C. to approximately 800° C.

Alternatively, the substrate may be heated to a sufficient temperature to obtain the desired silicon-containing film at a sufficient growth rate and with desired physical state and composition. A non-limiting exemplary temperature range to which the substrate may be heated includes from 50° C. to 600° C. Preferably, the temperature of the substrate remains less than or equal to 500° C.

Alternatively, the ALD process may be carried at a substrate temperature being set below a self-decomposition of the precursor. One of ordinary skill in the art would recognize how to determine the self-decomposition temperature of the precursor.

The reactor contains one or more substrates onto which the films will be deposited. A substrate is generally defined as the material on which a process is conducted. The substrates may be any suitable substrate used in semiconductor, photovoltaic, flat panel, or LCD-TFT device manufacturing. Examples of suitable substrates include wafers, such as silicon, silica, glass, plastic or GaAs wafers. The wafer may have one or more layers of differing materials deposited on it from a previous manufacturing step. For example, the wafers may include silicon layers (crystalline, amorphous, porous, etc.), silicon oxide layers, silicon nitride layers, silicon oxy nitride layers, carbon doped silicon oxide (SiCOH) layers, photoresist layers, anti-reflective layers, or combinations thereof. Additionally, the wafers may include copper layers or noble metal layers (e.g. platinum, palladium, rhodium, or gold). The layers may include oxides which are used as dielectric materials in MIM, DRAM, STT RAM, PC-RAM or FeRam technologies (e.g., $ZrO_2$ based materials, $HfO_2$ based materials, $TiO_2$ based materials, rare earth oxide based materials, ternary oxide based materials such as strontium ruthenium oxide (SRO), etc.) or from nitride-based films (e.g., TaN) that are used as an oxygen barrier between copper and the low-k layer. The wafers may include barrier layers, such as manganese, manganese oxide, etc. Plastic layers, such as poly(3,4-ethylenedioxythiophene)poly(styrenesulfonate) (PEDOT:PSS) may also be used. The layers may be planar or patterned. For example, the layer may be a patterned photoresist film made of hydrogenated carbon, for example $CH_x$, wherein x is greater than zero. The disclosed processes may deposit the silicon-containing layer directly on the wafer or directly on one or more than one (when patterned layers form the substrate) of the layers on top of the wafer. Furthermore, one of ordinary skill in the art will recognize that the terms "film" or "layer" used herein refer to a thickness of some material laid on or spread over a surface and that the surface may be a trench or a line. Throughout the specification and claims, the wafer and any associated layers thereon are referred to as substrates. In many instances though, the preferred substrate utilized may be selected from copper, silicon oxide, photoresist, hydrogenated carbon, TiN, SRO, Ru, and Si type substrates, such as polysilicon or crystalline silicon substrates. For example, a silicon nitride film may be deposited onto a Si layer. In subsequent processing, alternating silicon oxide and silicon nitride layers may be deposited on the silicon nitride layer forming a stack of multiple $SiO_2$/SiN layers used in 3D NAND gates. Furthermore, the substrate may be coated with patterned or unpatterned organic or inorganic films.

In addition to the disclosed Si-containing film forming compositions, a reactant may also be introduced into the reactor. The reactant may be an oxidizing agent, such as one of $O_2$, $O_3$, $H_2O$, $H_2O_2$; oxygen containing radicals, such as O. or OH., NO, $NO_2$; carboxylic acids such as formic acid, acetic acid, propionic acid, radical species of NO, $NO_2$, or the carboxylic acids; para-formaldehyde; and mixtures thereof. Preferably, the oxidizing agent is selected from the group consisting of $O_2$, $O_3$, $H_2O$, $H_2O_2$, oxygen containing radicals thereof such as O. or OH., and mixtures thereof. Preferably, when an ALD process is performed, the reactant is plasma treated oxygen, ozone, or combinations thereof. When an oxidizing agent is used, the resulting silicon containing film will also contain oxygen.

Alternatively, the reactant may be a nitrogen-containing reactant, such as one of $N_2$, $NH_3$, hydrazines (for example, $N_2H_4$, $MeHNNH_2$, MeHNNHMe), organic amines (for example, $N(CH_3)H_2$, $N(C_2H_5)H_2$, $N(CH_3)_2H$, $N(C_2H_5)_2H$, $N(CH_3)_3$, $N(C_2H_5)_3$, $(SiMe_3)_2NH$), pyrazoline, pyridine, diamine (such as ethylene diamine), radicals thereof, or mixtures thereof. When an N-containing source agent is used, the resulting silicon containing film will also contain nitrogen.

When a reducing agent is used, such as $H_2$, H radicals, but also other H-containing gases and precursors such as metal and metalloid hydrides, the resulting silicon containing film may be pure Si.

The reactant may be treated by plasma, in order to decompose the reactant into its radical form. $N_2$ may also be utilized when treated with plasma. For instance, the plasma may be generated with a power ranging from about 50 W to about 2000 W, preferably from about 100 W to about 500 W. The plasma may be generated or present within the reactor itself. Alternatively, the plasma may generally be at a location removed from the reactor, for instance, in a remotely located plasma system. One of skill in the art will recognize methods and apparatus suitable for such plasma treatment.

The Si-containing film forming compositions may also be used with a halosilane or polyhalodisilane, such as hexachlorodisilane, pentachlorodisilane, or tetrachlorodisilane, and one or more reactants to form Si, SiCN, or SiCOH films. PCT Publication Number WO2011/123792 discloses a SiN layer (not a Si or SiCOH layer), and the entire contents of which are incorporated herein in their entireties.

When the desired silicon-containing film also contains another element, such as, for example and without limitation, Ti, Hf, Zr, Ta, Nb, V, Al, Sr, Y, Ba, Ca, As, B, P, Sb, Bi, Sn, Ge lanthanides (such as Er), or combinations thereof, another precursor may include a metal-containing precursor which is selected from, but not limited to:

Metal Halides (e.g., $TiCl_4$, $TiI_4$, $TaCl_5$, $HfCl_4$, $ZrCl_4$, $AlCl_3$, $NbF_5$, etc.);
Alkyls (Al, Ge, Ga, In, Sb, Sn, Zn), such as trimethylaluminum, diethylzinc, triethylgalium;
Hydrides (GeH4, alanes, etc.);
Alkylamides (metals of group IV and V transition metals);
Imido group (metals of group V and VI);
Alkoxides (metals of group IV, V);
Cyclopentadienyls (Ru, Co, Fe, Group IV transition metals, lanthanides, etc.);
Carbonyls (ex: Ru, Co, Fe, Ni);
Amidinates and guanidinates (ex: Co, Mn, Ni, Cu, Sc, etc.);
Beta-diketonates (e.g.: Sc, Cu, lanthanides);
Beta-diketoimines (Cu, Ni, Co, etc.);
Bis-trialkylsilylamides (Ni, Co, Fe, etc.);
Oxo groups ($RuO_4$, $WOCl_4$, $PO(OEt)_3$, $AsO(OEt)_3$, etc.);
Heteroleptic molecules having a mixed set of ligands selected from the above families.

The Si-containing film forming compositions and one or more reactants may be introduced into the reaction chamber simultaneously (e.g., CVD), sequentially (e.g., ALD), or in other combinations. For example, the Si-containing film forming composition may be introduced in one pulse and two additional metal sources may be introduced together in a separate pulse (e.g., modified ALD). Alternatively, the reaction chamber may already contain the reactant prior to introduction of the Si-containing film forming composition. The reactant may be passed through a plasma system localized or remotely from the reaction chamber, and decomposed to radicals. Alternatively, the Si-containing film forming composition may be introduced to the reaction chamber continuously while other metal sources are introduced by pulse (e.g., pulsed-CVD). In each example, a pulse may be followed by a purge or evacuation step to remove excess amounts of the component introduced. In each example, the pulse may last for a time period ranging from about 0.01 s to about 20 s, alternatively from about 0.3 s to about 3 s, alternatively from about 0.5 s to about 2 s. In another alternative, the Si-containing film forming composition and one or more reactants may be simultaneously sprayed from a shower head under which a susceptor holding several wafers is spun (e.g., spatial ALD).

In a non-limiting exemplary ALD type process, the vapor phase of the Si-containing film forming composition is introduced into the reaction chamber, where it is contacted with a suitable substrate and forms a silicon-containing layer on the substrate. Excess composition may then be removed from the reaction chamber by purging and/or evacuating the reaction chamber. An oxygen source is introduced into the reaction chamber where it reacts with the silicon-containing layer in a self-limiting manner. Any excess oxygen source is removed from the reaction chamber by purging and/or evacuating the reaction chamber. If the desired film is a silicon oxide film, this two-step process may provide the desired film thickness or may be repeated until a film having the necessary thickness has been obtained.

Alternatively, if the desired film is a silicon metal oxide film (i.e., $SiMO_x$, wherein x may be 4 and M is Ti, Hf, Zr, Ta, Nb, V, Al, Sr, Y, Ba, Ca, As, B, P, Sb, Bi, Sn, Ge, lanthanides (such as Er), or combinations thereof), the two-step process above may be followed by introduction of a second vapor of a metal-containing precursor into the reaction chamber. The metal-containing precursor will be selected based on the nature of the silicon metal oxide film being deposited. After introduction into the reaction chamber, the metal-containing precursor is contacted with the silicon oxide layer on the substrate. Any excess metal-containing precursor is removed from the reaction chamber by purging and/or evacuating the reaction chamber. Once again, an oxygen source may be introduced into the reaction chamber to react with the metal-containing precursor. Excess oxygen source is removed from the reaction chamber by purging and/or evacuating the reaction chamber. If a desired film thickness has been achieved, the process may be terminated. However, if a thicker film is desired, the entire four-step process may be repeated. By alternating the provision of the Si-containing film forming compositions, metal-containing precursor, and oxygen source, a film of desired composition and thickness may be deposited.

Additionally, by varying the number of pulses, films having a desired stoichiometric M:Si ratio may be obtained. For example, a $SiMO_2$ film may be obtained by having one pulse of the mono-substituted TSA precursor and one pulses of the metal-containing precursor, with each pulse being followed by pulses of the oxygen source. However, one of ordinary skill in the art will recognize that the number of pulses required to obtain the desired film may not be identical to the stoichiometric ratio of the resulting film.

In a non-limiting exemplary PE-ALD type process, the vapor phase of the Si-containing film forming composition is introduced into the reaction chamber, where it is contacted with a suitable substrate, while a low reactivity oxygen source, such as $O_2$, is continuously flowing to the chamber. Excess composition may then be removed from the reaction chamber by purging and/or evacuating the reaction chamber. A plasma is then lit to activate the oxygen source to react with the absorbed mono-substituted TSA precursor in a self-limiting manner. The plasma is then switched off and the flow of the Si-containing film forming composition may proceed immediately after. This two-step process may provide the desired film thickness or may be repeated until a silicon oxide film having the necessary thickness has been obtained. The silicon oxide film may contain some C impurities, typically between 0.005% and 2%. The oxygen gas source and the substrate temperature may be selected by one of ordinary skill in the art so as to prevent reaction between the oxygen source and the mono-substituted TSA when the plasma is off. Dialkylamino-substituted TSA are particularly suitable for such a process, and are preferably $(SiH_3)_2N$—$SiH_2$—$NEt_2$, $(SiH_3)_2N$—$SiH_2$—$NiPr_2$ or $(SiH_3)_2N$—$SiH_2$—$NHR$, R being -tBu or —$SiMe_3$.

In another non-limiting exemplary PE-ALD type process, the vapor phase of the Si-containing film forming compositions is introduced into the reaction chamber, where it is contacted with a suitable substrate, while a low reactivity nitrogen source, such as $N_2$, is continuously flowing to the chamber. Excess composition may then be removed from the reaction chamber by purging and/or evacuating the reaction chamber. A plasma is then lit to activate the nitrogen source to react with the absorbed mono-substituted TSA precursor in a self-limiting manner. The plasma is then switched off and flow of the Si-containing film forming composition may proceed immediately after. This two-step process may provide the desired film thickness or may be repeated until a silicon nitride film having the necessary thickness has been obtained. The silicon nitride film may contain some C impurities, typically between 0.5% and 10%. The nitrogen gas source and the substrate temperature may be selected by one of ordinary skill in the art so as to prevent reaction between the nitrogen source and the mono-substituted TSA when the plasma is off. Amino-substituted TSA and mono-halo TSA are particularly suitable for such a process, and are preferably $(SiH_3)_2N$—$SiH_2$—Cl, $(SiH_3)_2N$—$SiH_2$—$NEt_2$, $(SiH_3)_2N$—$SiH_2$—$NiPr_2$, $(SiH_3)_2N$—$SiH_2$—$NHR$, R being -tBu or —$SiMe_3$, or $(SiH_3)_2N$—$SiH_2$—$N(SiH_3)_2$.

In a non-limiting exemplary LPCVD type process, the vapor phase of the Si-containing film forming compositions, preferably containing a mono-halo substituted TSA precursor, is introduced into the reaction chamber holding the substrates and kept at a pressure typically between 0.1 and 10 torr, and more preferably between 0.3 and 3 torr, and at a temperature between 250° C. and 800° C., preferably between 350° C. and 600° C., where it is mixed with a reactant, typically $NH_3$. A thin conformal SiN film may thus be deposited on the substrate(s). One of ordinary skill in the art will recognize that the Si/N ratio in the film may be tuned by adjusting the mono-substituted TSA precursor and N-source flow rates.

In another alternative, dense SiN films may be deposited using an ALD method with hexachlorodisilane (HCDS), pentachlorodisilane (PODS), monochlorodisilane (MCDS), dichlorodisilane (DCDS) or monochlorosilane (MCS), the disclosed Si-containing film forming compositions, and an ammonia reactant. The reaction chamber may be controlled at 5 Torr, 550° C., with a 55 sccm continuous flow of Ar. An approximately 10 second long pulse of the disclosed Si-containing film forming composition at a flow rate of approximately 1 sccm is introduced into the reaction chamber. The composition is purged from the reaction chamber with an approximately 55 sccm flow of Ar for approximately 30 seconds. An approximately 10 second pulse of HCDS at a flow rate of approximately 1 sccm is introduced into the reaction chamber. The HCDS is purged from the reaction chamber with an approximately 55 sccm flow of Ar for approximately 30 seconds. An approximately 10 second long pulse of $NH_3$ at a flow rate of approximately 50 sccm is introduced into the reaction chamber. The $NH_3$ is purged from the reaction chamber with an approximately 55 sccm flow of Ar for approximately 10 seconds. These 6 steps are repeated until the deposited layer achieves a suitable thickness. One of ordinary skill in the art will recognize that the introductory pulses may be simultaneous when using a spatial ALD device. As described in PCT Pub No WO2011/123792, the order of the introduction of the precursors may be varied and the deposition may be performed with or without the $NH_3$ reactant in order to tune the amounts of carbon and nitrogen in the SiCN film. One of ordinary skill in the art would further recognize that the flow rates and pulse times may vary amongst different deposition chambers and would be able to determine the necessary parameter for each device.

In a non-limiting exemplary process, the vapor phase of the disclosed Si-containing film forming compositions, preferably containing mono-halo substituted TSA, is introduced into the reaction chamber holding a substrate having a porous low-k film. A pore sealing film may be deposited in the conditions described in US 2015/0004806 (i.e., by introducing the disclosed silicon-containing film forming composition, an oxidant (such as ozone, hydrogen peroxide, oxygen, water, methanol, ethanol, isopropanol, nitric oxide, nitrous dioxide, nitrous oxide, carbon monoxide, or carbon dioxide), and a halogen free catalyst compound (such as nitric acid, phosphoric acid, sulfuric acid, ethylenediaminetetraacetic acid, picric acid, or acetic acid) to a reaction chamber and exposing the substrate to the process gases under conditions such that a condensed flowable film forms on the substrate).

In yet another alternative, a silicon-containing film may be deposited by the flowable PECVD method disclosed in U.S. Patent Application Publication No. 2014/0051264 using the disclosed compositions and a radical nitrogen- or oxygen-containing reactant. The radical nitrogen- or oxygen-containing reactant, such as $NH_3$ or $H_2O$ respectively, is generated in a remote plasma system. The radical reactant and the vapor phase of the disclosed precursors are introduced into the reaction chamber where they react and deposit the initially flowable film on the substrate. Applicants believe that the nitrogen atoms of the $(SiH_3)_2N$—$(SiH_2$—X) structure helps to further improve the flowability of the deposited film, resulting in films having less voids, especially when X is an amino group, and more specifically when X is a disilylamino group like —$N(SiH_3)_2$.

The silicon-containing films resulting from the processes discussed above may include $SiO_2$, nitrogen doped silicon oxide, SiN, SiON, SiCN, SiCOH, or $MSiN_yO_x$, wherein M is an element such as Ti, Hf, Zr, Ta, Nb, V, Al, Sr, Y, Ba, Ca, As, B, P, Sb, Bi, Sn, Ge, and x, y may be from 0-4 and y+x=4, depending of course on the oxidation state of M. One of ordinary skill in the art will recognize that by judicial selection of the appropriate mono-substituted TSA precursor and reactants, the desired film composition may be obtained.

Upon obtaining a desired film thickness, the film may be subject to further processing, such as thermal annealing, furnace-annealing, rapid thermal annealing, UV or e-beam curing, and/or plasma gas exposure. Those skilled in the art recognize the systems and methods utilized to perform these additional processing steps. For example, the silicon-containing film may be exposed to a temperature ranging from approximately 200° C. and approximately 1000° C. for a time ranging from approximately 0.1 second to approximately 7200 seconds under an inert atmosphere, a H-containing atmosphere, a N-containing atmosphere, an O-containing atmosphere, or combinations thereof. Most preferably, the temperature is 600° C. for less than 3600 seconds under a reactive H-containing atmosphere. The resulting film may contain fewer impurities and therefore may have improved performance characteristics. The annealing step may be performed in the same reaction chamber in which the deposition process is performed. When the deposition process is a FCVD, the curing step is preferably an oxygen curing step, carried out at a temperature lower than 600° C. The oxygen containing atmosphere may contain $H_2O$ or $O_3$. Alternatively, the substrate may be removed from the reaction chamber, with the annealing/flash annealing process being performed in a separate apparatus.

EXAMPLES

The following non-limiting examples are provided to further illustrate embodiments of the invention. However, the examples are not intended to be all inclusive and are not intended to limit the scope of the inventions described herein.

The examples described herein are TSA based precursors, i.e., mono-substituted TSA.

Example 1: Synthesis of $(SiH_3)_2N$—$SiH_2$—$NiPr_2$ and of $(SiH_3)_2N$—$SiH_2$—$NEt_2$ 300 g of diisopropylamine (3.0 mol) was charged to a 1-liter filter flask equipped with an overhead mechanical stirrer, a nitrogen bubbler, a chiller and a hydride scrubber as a reactor. 60 g (0.4 mol) of chlorotrisilylamine was charged to a dropping funnel. The dropping funnel was affixed to the reactor. A nitrogen sweep was added to the dropping funnel to prevent salt formation in the tip of the funnel. The chiller was set to 18° C. and the chlorotrisilylamine was added via dropping funnel over a 1.5 hr period. The reactor temperature was set at 22-23° C. during the addition. The reactor was allowed to stir for 0.5 hr after the addition was complete.

The amine hydrochloride salt was then filtered. The filter cake was rinsed with two 50 ml aliquots of diisopropylamine. The majority of the diisopropylamine was distilled off leaving 72 g of a crude product. The crude product was combined with other crude products from several smaller scale preparations of $(SiH_3)_2N$—$SiH_2$—$NiPr_2$ done in a similar fashion. $(SiH_3)_2N$—$SiH_2$—$NiPr_2$ was then distilled at 86° C. under a vacuum of −28 inches of mercury and 79 g of >99% pure product was collected. The overall yield was 56%. Table 2 shows vapor pressure data of $(SiH_3)_2N$—$SiH_2$—$NiPr_2$ estimated from the distillation and TSU data.

TABLE 2

Vapor pressure data of $(SiH_3)_2N$—$SiH_2$—$NiPr_2$

| Temperature (° C.) | Pressure (torr) |
|---|---|
| 86 | 38 |
| 100 | 72 |
| 150 | 140 |

The synthesis of $(SiH_3)_2N$—$SiH_2$—$NEt_2$ proceeds similarly with the same molar ratio, but replaces diisopropylamine with diethylamine.

Example 2: Synthesis of $(SiH_3)_2N$—$SiH_2$—$NHiPr$ 300 g of isopropylamine (3.0 mol) was charged to a 1-liter filter flask equipped with an overhead mechanical stirrer, a nitrogen bubbler, a chiller and a hydride scrubber as a reactor. 60 g (0.4 mol) of chlorotrisilylamine was charged to a dropping funnel. The dropping funnel was affixed to the reactor. A nitrogen sweep was added to the dropping funnel to prevent salt formation in the tip of the funnel. The chiller was set to 18° C. and the chlorotrisilylamine was added via dropping funnel over a 1.5 hr period. The reactor temperature was set at 22-23° C. during the addition. The reactor was allowed to stir for 0.5 hr after the addition was complete. The amine hydrochloride salt was then filtered. The filter cake was rinsed with two 50 mL aliquots of isopropylamine. The majority of the isopropylamine was distilled off leaving 72 g of a crude product. The crude product was combined with other crude products from several smaller scale preparations of $(SiH_3)_2N$—$SiH_2$—$NHiPr$ done in a similar fashion. $(SiH_3)_2N$—$SiH_2$—$NHiPr$ was then distilled at 86° C. under a vacuum of −28 inches of mercury and 79 g of >99% pure product was collected.

Example 3: Synthesis of $(SiH_3)_2N$—$SiH_2$—$Br$ and of $(SiH_3)_2N$—$SiH_2$—$N(SiH_3)_2$ $(SiH_3)_2N$—$SiH_2$—$Br$ and $(SiH_3)_2N$—$SiH_2$—$N(SiH_3)_2$ may be obtained by $SnBr_4$ reacts with TSA: $SnBr_4+H_3SiN(SiH_3)_2=BrH_2SiN(SiH_3)_2+(SiH_3)_2N$—$SiH_2$—$N(SiH_3)_2+SnBr_2+HBr$. A side product of the above reaction, HBr, may then be removed by a reaction with the starting material TSA, i.e., $N(SiH_3)_3+4HBr=NH_4Br+3BrSiH_3$. The synthesis process is as follows.

A round bottom flask with a PTFE-coated magnetic stir egg was charged with stoichiometric excess of TSA. If necessary, a solvent (e.g., dodecane) and an HBr scavenger (e.g., tributylamine) may be added to the flask prior to adding TSA. The flask was fitted with a cold finger condenser or a distillation head. A liquid addition funnel was attached to the flask and charged with a solution of $SnBr_4$ in a solvent (such as, anisole or dodecane). The flask may then be cooled down and the $SnBr_4$ solution was added dropwise to the flask. The headspace of the flask may be kept under atmospheric pressure of nitrogen or at a reduced pressure in order to remove HBr as it forms.

After the addition was finished, the volatile products may be collected by pulling vacuum through trap(s). The collected volatile products may then be analyzed by GCMS. It was found that $(SiH_3)_2N(SiH_2Br)$ and $(SiH_3)_2N(SiH_2N(SiH_3)_2)$ were formed upon treating TSA with $SnBr_4$. The following byproducts were also identified: silane, bromosilane, dibromotrisilylamine. The solvents and unreacted $SnBr_4$ (in some cases) were also found.

The resulting $(SiH_3)_2N$—$SiH_2$—$N(SiH_3)_2$ was liquid at room temperature (~22° C.), with a melting point of approximately −106° C. and a boiling point of approximately 131° C. The vapor pressure was calculated to be ~8 hPa at 27° C.

Example 4

The following PEALD testing was performed using a Picosun R200 PEALD 8" deposition tool with a 4" wafer. The vapor of the mono-substituted TSA precursor was delivered to the Picosun tool as shown in FIG. 1.

Figure 2:
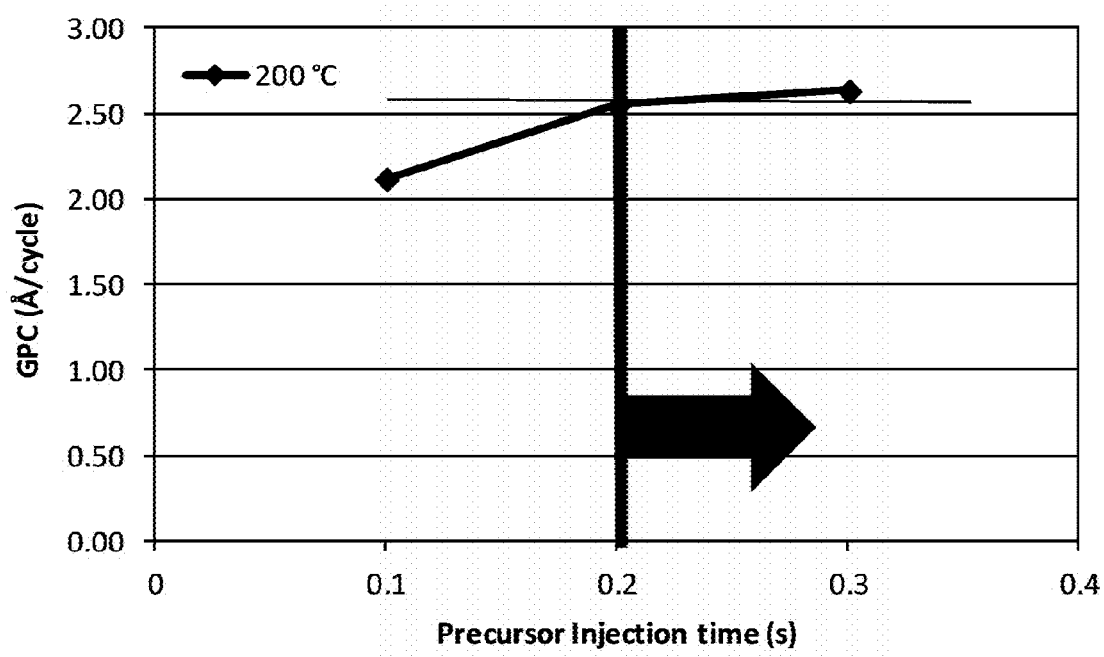
FIG. 2 is a graph the ALD growth rate of silicon oxide films as a function of the number of precursor pulses using the precursor (SiH$_3$)$_2$N—SiH$_2$—NiPr$_2$.

ALD tests were performed using the $(SiH_3)_2N$—$SiH_2$—$NiPr_2$, which was placed in an ampoule heated to 70° C. and $O_2$ plasma as oxidizing reactant. Typical ALD conditions were used with the reactor pressure fixed at ~9 hPa (1 hPa=100 Pa=1 mbar). Two 0.1-second pulses of the precursor vapor were introduced into the deposition chamber via overpressure in the ampoule using the 3-way pneumatic valve. The 0.1-second pulses were separated by a 0.5 second pause. A 4-second N2 purge removed any excess precursor. A 16-second plasma O2 pulse was followed by a 3-second N2 purge. The process was repeated until a minimum thickness of 300 Angstrom was obtained. Depositions were performed with the substrate heated to 70° C., 150° C., and 300° C. Real self limited ALD growth behavior was validated as shown in FIG. 2 by increasing the number of precursor pulses within a given cycle.

Figure 3:
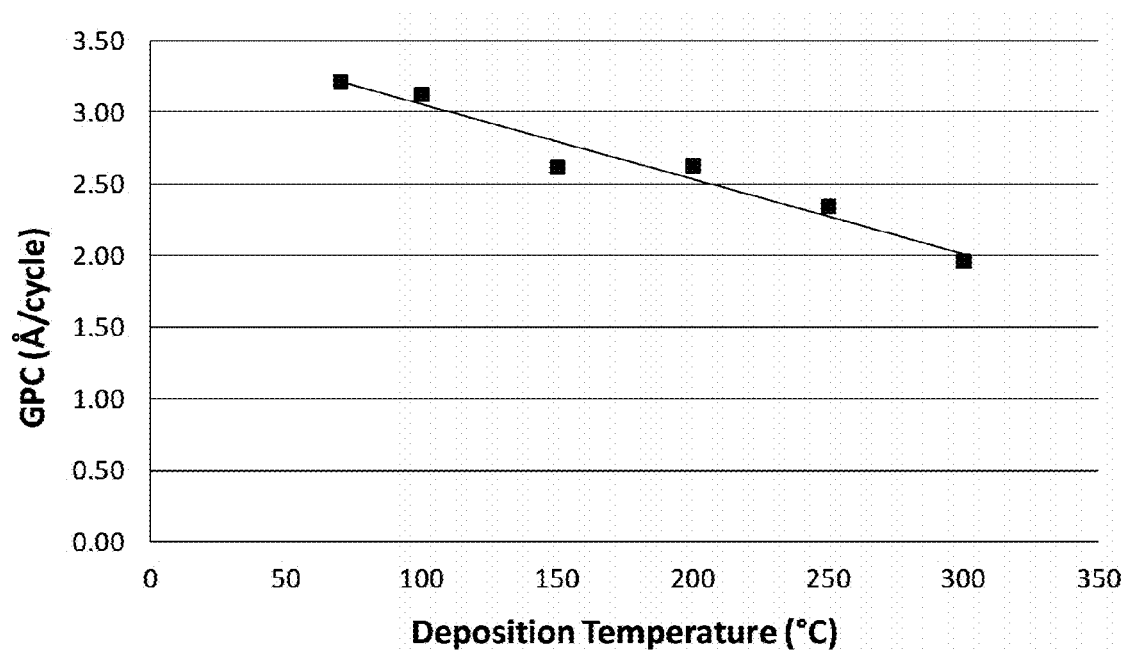
FIG. 3 is a graph of the ALD growth rate of silicon oxide thin film as a function of the temperature using the precursor (SiH$_3$)$_2$N—SiH$_2$—NiPr$_2$.

ALD tests were also performed using the prior art $SiH_2(NEt_2)_2$ precursor, which was placed in an ampoule heated to 60° C. and $O_2$ plasma as oxidizing reactant. Applicants believe that $SiH_2(NEt_2)_2$ is currently used to deposit $SiO_2$ in several commercial processes. Typical ALD conditions were used with the reactor pressure fixed at ~9 hPa (1 hPa=100 Pa=1 mbar). Two 0.1-second pulses of the precursor vapor were introduced into the deposition chamber via overpressure in the ampoule using the 3-way pneumatic valve. The 0.1-second pulses were separated by a 0.5 second pause. A 4-second $N_2$ purge removed any excess precursor. A 16-second plasma O2 pulse was followed by a 3-second $N_2$ purge. The process was repeated until a minimum thickness of 300 Ang was reached. Depositions were performed at 70° C., 150° C., 200° C., and 300° C. As shown in FIG. 3, the growth per cycle decreased with increasing temperature.

Table 1 summarizes the results:

|  | $SiH_2(NEt_2)_2$ | $(SiH_3)_2N$—$SiH_2$—$NiPr_2$ |
|---|---|---|
| Growth rate 70° C.[1] | 1.42 Ang/cycle | 3.10 Ang/cycle |
| Growth rate 300° C.[1] | 0.98 Ang/cycle | 2.05 Ang/cycle |
| Wet Etch Rate 70° C.[2] | 9.4 Ang/sec | 8.8 Ang/sec |
| Wet Etch Rate 150° C.[2] | 7.2 Ang/sec | 6.7 Ang/sec |
| Wet Etch Rate 300° C.[2] | 6.6 Ang/sec | 6.7 Ang/sec |
| Refractive Index 70° C.[3] | 1.432 | 1.460 |
| Atomic % Carbon 70° C.[4] | 0.05% | TBD |
| Atomic % Carbon 150° C.[4] | 0.045% | 0.015-0.03% |
| Atomic % Hydrogen 150° C.[4] | ~10% | ~10% |
| Atomic % Nitrogen 150° C.[4] | 0.015% | 0.1% |
| Within Wafer Non Uniformity[5] | 2.84% | 2.90% |

[1]Growth rate for films deposited at the stated temperatures
[2]Wet Etch Rate for films deposited at the stated temperatures
[3]Refractive index for film deposited at 70° C.
[4]Atomic percentage in a film deposited at the stated temperature as determined by Secondary Ion Mass Spectrometry (SIMS). Hydrogen content is subject to uncertainty when measured by SIMS, as one skilled in the art would recognize.
[5]Within Wafer Non Uniformity of a film deposited at 200° C. as determined by ellipsometer over a 6 inch silicon wafer. This parameter was not optimized and better uniformity would be expected from an industrial tool.

As can be seen, the growth rate for films produced by $(SiH_3)_2N$—$SiH_2$—$NiPr_2$ is much better than those of $SiH_2$ (NEt$_2$)$_2$ at both 70° C. and 300° C. At 70° C., (SiH$_3$)$_2$N—SiH$_2$—NiPr$_2$ has a much better wet etch rate and refractive index than SiH$_2$(NEt$_2$)$_2$, which both indicate formation of a much better, denser oxide film.

Example 5

ALD tests to deposit N-doped silicon oxide were performed using the (SiH$_3$)$_2$N—SiH$_2$—NiPr$_2$, which was placed in an ampoule heated to 70° C., O$_2$ plasma as oxidizing reactant and NH$_3$ plasma as an additional reactant. Typical ALD conditions were used with the reactor pressure fixed at ~9 hPa. Two 0.1-second pulses of the precursor vapor were introduced into the deposition chamber via overpressure in the ampoule using the 3-way pneumatic valve. The 0.1-second pulses were separated by a 0.5 second pause. A 4-second N$_2$ purge removed any excess precursor. A 16-second plasma O$_2$ pulse was followed by a 3-second N2 purge. Two 0.1-second pulses of the precursor vapor were introduced into the deposition chamber via overpressure in the ampoule using the 3-way pneumatic valve. The 0.1-second pulses were separated by a 0.5 second pause. A 4-second N$_2$ purge removed any excess precursor. An 11-second plasma NH$_3$ pulse was followed by a 3-second purge. The entire process (precursor-plasma O$_2$-precursor-plasma NH$_3$) was repeated until the thickness reached at least 300 Ang. Depositions were performed at 150° C.

The resulting SiO$_2$ film had a wet etch rate of 3.2 Ang/sec and N concentration of ~1%. Such a low etch rate is found to be beneficial for spacer-based double patterning to enable a low edge roughness in the transfer layer when the ALD-deposited silicon oxide film is used as a mask. The person ordinary skilled in the art would recognize that the Oxygen to Nitrogen content in the obtained film can be tuned by adjusting the number, sequence or/and duration of the O containing reactant and N containing reactant pulses. Applicant believes that a N concentration of approximately 0.5% to approximately 5% in an SiO$_2$ film is beneficial for the spacer-defined patterning applications.

Example 6

Figure 4:
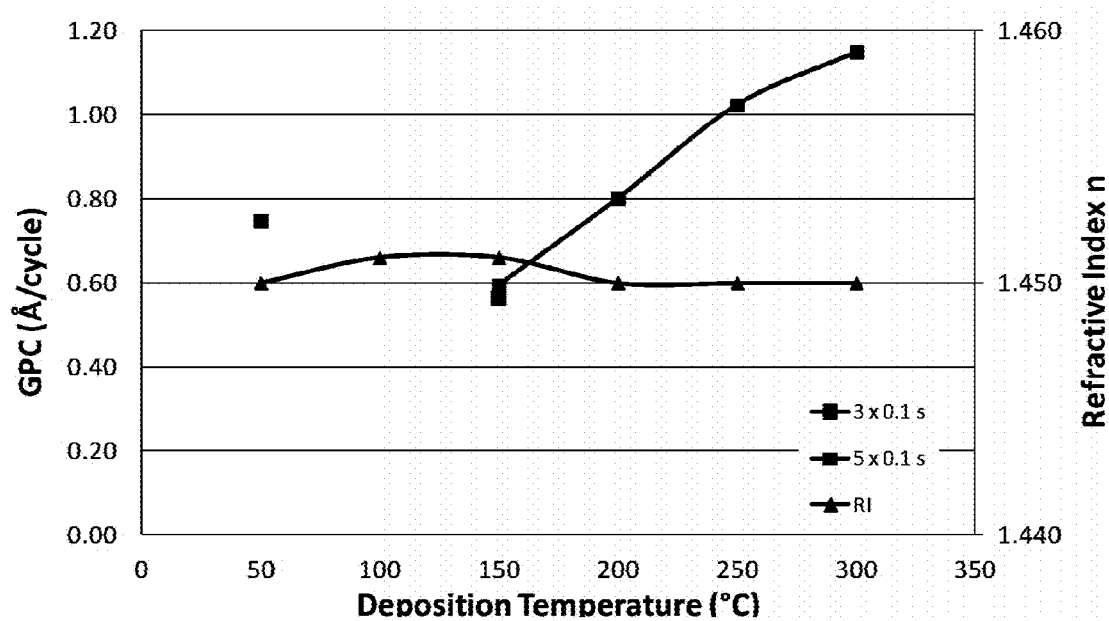
FIG. 4 is is a graph the ALD growth rate of silicon oxide films as a function of the number of precursor pulses and the temperature using the precursor (SiH$_3$)$_2$N—SiH$_2$—N(SiH$_3$)$_2$.

ALD tests were performed using the (SiH$_3$)$_2$N—SiH$_2$—N(SiH$_3$)$_2$, which was placed in an ampoule heated to 26° C. and O$_2$ plasma as oxidizing reactant. Typical ALD conditions were used with the reactor pressure fixed at ~9 hPa. Three 0.1-second pulses of the precursor vapor were introduced into the deposition chamber via overpressure in the ampoule using the 3-way pneumatic valve. The 0.1-second pulses were separated by a 0.5 second pause. A 4-second N$_2$ purge removed any excess precursor. A 16-second plasma O$_2$ pulse was followed by a 3-second N$_2$ purge. The entire process (precursor-plasma O2-) was repeated until the thickness reached at least 300 Ang. As shown in FIG. 4, the growth per cycle increased with increasing deposition temperatures from 150° C. to 300° C. FIG. 4 also shows comparative growth per cycle results of five 0.1-second pulses versus three 0.1-second pulses. Both were approximately 0.6 A/cycle, indicating true ALD saturation because the larger amounts of precursor introduced via 5 pulses do not result in a higher growth rate than the film produced by 3 pulses.

The growth rate was approximately 0.58 Ang/cycle at 150° C. and resulted in a film having a refractive index of 1.45. For comparison, attempts to grow an SiO$_2$ film by ALD using pure TSA in similar conditions have not yielded any films, thus proving the benefit of the chemical functionalization to enhance the reactivity with the surface hydroxyl groups.

While embodiments of this invention have been shown and described, modifications thereof may be made by one skilled in the art without departing from the spirit or teaching of this invention. The embodiments described herein are exemplary only and not limiting. Many variations and modifications of the composition and method are possible and within the scope of the invention. Accordingly the scope of protection is not limited to the embodiments described herein, but is only limited by the claims which follow, the scope of which shall include all equivalents of the subject matter of the claims.

What is claimed is:

1. A Si-containing film forming composition comprising a mono-substituted TSA precursor having the formula:

(SiH$_3$)$_2$N—SiH$_2$—X wherein X is selected from an isocyanato group [—NCO]; an amino group [—NR$^1$R$^2$]; an N-containing C$_4$-C$_{10}$ saturated or unsaturated heterocycle; or an alkoxy group [—O—R]; R$^1$, R$^2$ and R each is selected from H; a C$_1$-C$_6$ linear or branched, saturated or unsaturated hydrocarbyl group; provided that if R$^1$=H, then R$^2$≠H or Me.

2. The Si-containing film forming composition of claim 1, wherein X=NR$^1$R$^2$ and R$^1$ and R$^2$ each is independently selected from H, Me, Et, or iPr.

3. The Si-containing film forming composition of claim 2, wherein the mono-substituted TSA precursor is (SiH$_3$)$_2$N—SiH$_2$—NiPr$_2$.

4. The Si-containing film forming composition of claim 2, wherein the mono-substituted TSA precursor is (SiH$_3$)$_2$N—SiH$_2$—NEt$_2$.

5. The Si-containing film forming composition of claim 2, wherein the mono-substituted TSA precursor is (SiH$_3$)$_2$N—SiH$_2$—NHiPr.

6. The Si-containing film forming composition of claim 1, wherein X is —O—SiR$_3$, and each R is independently selected from H or a C$_1$-C$_4$ hydrocarbyl group.

7. The Si-containing film forming composition of claim 6, the precursor being (SiH$_3$)$_2$—N—SiH$_2$—O—SiMe$_3$.

8. A method for forming a Si-containing film, the method comprising the steps of:

introducing into a reactor containing a substrate a vapor including a mono-substituted TSA precursor having a formula (SiH$_3$)$_2$N—SiH$_2$—X, wherein X is selected from a an isocyanato group [—NCO]; an amino group [—NR$^1$R$^2$]; a N-containing C$_4$-C$_{10}$ saturated or unsaturated heterocycle; or an alkoxy group —O—R; R$^1$, R$^2$ and R each is selected from H; a C$_1$-C$_6$ linear or branched, saturated or unsaturated hydrocarbyl group; or a silyl group SiR'$_3$ with each R' being independently selected from H; a halogen atom selected from Cl, Br, or I; a C$_1$-C$_4$ saturated or unsaturated hydrocarbyl group; a C$_1$-C$_4$ saturated or unsaturated alkoxy group; or an amino group —NR$^3$R$^4$ with each R$^3$ and R$^4$ being selected from H or a C$_1$-C$_6$ linear or branched, saturated or unsaturated hydrocarbyl group, provided that if R$^1$=H, then R$^2$≠H or Me;

depositing at least part of the mono-substituted TSA precursor onto the substrate to form the silicon-containing film on the substrate using a vapor deposition process.

9. The method of claim 8, wherein R$^1$ and R$^2$ each is independently selected from Me, Et, and iPr.

10. The method of claim 9, wherein the mono-substituted TSA precursor is $(SiH_3)_2N—SiH_2—NiPr_2$.

11. The method of claim 9, wherein the mono-substituted TSA precursor is $(SiH_3)_2N—SiH_2—NEt_2$.

12. The method of claim 9, wherein the mono-substituted TSA precursor is $(SiH_3)_2N—SiH_2—NHiPr$.

13. The method of claim 8, wherein X is $—O—SiR_3$ and each R is independently selected form H or a $C_1$-$C_4$ hydrocarbyl group.

14. The method of claim 8, wherein the vapor deposition process is atomic layer deposition or chemical vapor deposition.

15. The method of claim 8, further comprising the step of delivering into the reactor a reactant.

16. The method of claim 15, wherein the reactant is selected from the group consisting of $O_2$, $O_3$, $H_2O$, $H_2O_2$, NO, $NO_2$, $N_2O$, alcohols, diols, carboxylic acids, ketones, ethers, O atoms, O radicals, O ions, ammonia, $N_2$, N atoms, N radicals, N ions, saturated or unsaturated hydrazine, amines, diamines, ethanolamine, $H_2$, H atoms, H radicals, H ions, and combinations thereof.

17. The method of claim 8, further comprising the step of delivering into the reactor a second vapor including a second precursor.

18. The method of claim 17, wherein an element of the second precursor is selected from the group consisting of Ti, Hf, Zr, Ta, Nb, V, Al, Sr, Y, Ba, Ca, As, B, P, Sb, Bi, Sn, Ge, and combinations thereof.

19. The method of claim 8, wherein the substrate is selected from the group consisting of a silicon wafer, a glass substrate, and a plastic substrate.

20. The method of claim 19, wherein the substrate is coated with patterned or unpatterned organic or inorganic films.

21. The method of claim 16, further comprising the step of delivering into the reactor a second reactant, the second reactant being different than the reactant, the second reactant selected from the group consisting of $O_2$, $O_3$, $H_2O$, $H_2O_2$, NO, $NO_2$, $N_2O$, alcohols, diols, carboxylic acids, ketones, ethers, O atoms, O radicals, O ions, ammonia, $N_2$, N atoms, N radicals, N ions, saturated or unsaturated hydrazine, amines, diamines, ethanolamine, $H_2$, H atoms, H radicals, H ions, and combinations thereof.

22. A nitrogen-doped silicon oxide film, the film formed by the process of:
   introducing into a reactor containing a substrate a vapor including a mono-substituted TSA precursor to form a silicon-containing layer on the substrate, the mono-substituted TSA precursor having a formula $(SiH_3)_2N—SiH_2—X$, wherein X is selected from a halogen atom selected from Cl, Br or I; an isocyanato group [—NCO]; an amino group [—$NR^1R^2$]; a N-containing $C_4$-$C_{10}$ saturated or unsaturated heterocycle; or an alkoxy group [—O—R]; $R^1$, $R^2$ and R each is selected from H; a $C_1$-$C_6$ linear or branched, saturated or unsaturated hydrocarbyl group; or a silyl group $SiR'_3$ with each R' being independently selected from H; a halogen atom selected from Cl, Br, or I; a $C_1$-$C_4$ saturated or unsaturated hydrocarbyl group; a $C_1$-$C_4$ saturated or unsaturated alkoxy group; or an amino group —$NR^3R^4$ with each $R^3$ and $R^4$ being selected from H or a $C_1$-$C_6$ linear or branched, saturated or unsaturated hydrocarbyl group, provided that if $R^1$=H, then $R^2 \neq H$ or Me;
   reacting an oxidizing agent with the silicon-containing layer to form an oxidized silicon-containing layer by introducing the oxidizing agent into the reactor;
   reacting the mono-substituted TSA precursor with the oxidized silicon-containing layer to form a silicon-rich oxidized silicon-containing layer by introducing the mono-substituted TSA precursor into the reactor;
   reacting a nitrogen-containing reactant with the silicon-containing layer to form the nitrogen-doped silicon oxide film by introducing the nitrogen-containing reactant into the reactor.

23. The method of claim 22, further comprising purging the reactor with an inert gas between each introduction step.

24. The method of claim 22, wherein the mono-substituted TSA precursor is $(SiH_3)_2N—SiH_2—NiPr_2$.

25. The method of claim 22, wherein the mono-substituted TSA precursor is $(SiH_3)_2N—SiH_2—NEt_2$.

26. The method of claim 22, wherein the mono-substituted TSA precursor is $(SiH_3)_2N—SiH_2—NHiPr$.

27. The method of claim 22, wherein the mono-substituted TSA precursor is $(SiH_3)_2N—SiH_2—N(SiH_3)_2$.

* * * * *